United States Patent
Cochran et al.

(10) Patent No.: US 6,410,311 B1
(45) Date of Patent: Jun. 25, 2002

(54) RECOMBINANT FELINE HERPESVIRUS COMPRISING A FOREIGN DNA INSERTED INTO A REGION CORRESPONDING TO A 3.0 KB ECORI-SALI FRAGMENT OF A FELINE HERPESVIRUS GENOME

(75) Inventors: Mark D. Cochran, Carlsband; Barbara J. Winslow, Delmar, both of CA (US)

(73) Assignee: Schering-Plough Veterinary Corporation, Reno, NV (US)

(*) Notice: Subject to any disclaimer, the term of this patent is extended or adjusted under 35 U.S.C. 154(b) by 0 days.

(21) Appl. No.: 08/854,110

(22) Filed: May 9, 1997

(51) Int. Cl.[7] .............. A61K 39/29; C12Q 1/70
(52) U.S. Cl. .............. 435/320.1; 435/5; 435/69.3; 435/471; 435/235.1; 435/236.1; 435/948; 424/184.1; 424/199.1; 424/229.1
(58) Field of Search ............... 435/320.1, 69.3, 435/235.1, 236; 424/184.1, 199.1, 229.1

(56) References Cited

U.S. PATENT DOCUMENTS 5,223,424 A * 6/1993 Cochran et al.
5,558,867 A   9/1996 Sakaguchi et al.

FOREIGN PATENT DOCUMENTS

EP        0576092     * 6/1993
WO        9500172     * 1/1995

OTHER PUBLICATIONS

Sussman et al. Virol. 214:12–20, 1995.*
Kruger, J.M. et al. (1996) *Virology* 220:299–308 (Exhibit C).
Rota, P.A. et al. (1986) *Virology* 154:168–179 (Exhibit D).
Spatz, S. J. et al. (1994) *J. of Gen. Virol.* 75:1235–1244 (Exhibit E);and.
Spatz, S.J. and Maes, R. K. (1993) *Virology* 197:125–136 (Exhibit F).

* cited by examiner

*Primary Examiner*—Mary K. Zeman
(74) *Attorney, Agent, or Firm*—Pamela G. Salkeld

(57) ABSTRACT

This invention provides a recombinant feline herpesvirus comprising a foreign DNA inserted into a feline herpesvirus genome, wherein the foreign DNA is inserted into a region of the genome which corresponds to the 3.0 kb EcoRI-SalI fragment within a SalI A fragment of the feline herpesvirus genome and is capable of being expressed in a host cell into which the virus is introduced. Further this invention provides a recombinant feline herpesvirus comprising a feline herpesvirus genome, wherein the feline herpesvirus genome contains a deletion in a SacII site within the 3.0 kb EcoRI-SalI fragment of the SalI A fragment of the feline herpesvirus genome. Lastly, this invention provides vaccines and methods of immunization of animals infected with feline herpesvirus.

25 Claims, 7 Drawing Sheets

Junction A  [Eco RI] [Eco RI]
GAAT ACA CGG AAT TAA TTC GAT GCC ACA ATC GC
← pSP 65    FHV Sal I A →

Junction B  [Sac II] [Sal I]
AAA GGC TGC TGC CTC GAC GTC TGG GG
← FHV Sal I A    PRV BamHI#10 →

Junction E  [Sal I] [Sac II]
GCC TGG TGT CCG TCG AGG CAG CTTT CCT AGG GAG
← PRV BamHI#7    FHV Sal I A →

Junction F  [Sal I]  [EcoRI]
TCC GTA CTA TCT ATT GTC GAA ATT CGA GCT CGC CCG GGG ATCC
← FHV Sal I A    pSP 65 →

FIG.

Junction A

[Eco RI] [Eco RI]
GAAT ACA CGG AAT TAA TTC GAT GCC ACA ATC GC
  pSP 65 ←——→ FHV Sal I A

Junction B

[Nde I]   [Sal I]
TG ACA CTC CAT TGG CATC GA CGG ACA CCA GGC GCCG

FHV Sal I A PRV BamHI#7

Junction E

[Sal I] [Nde I]

GCG CCC CAG ACG TCG ATG AAA CAA ACC TAG CCA TAGA

PRV BamHI#10 FHV Sal I A

Junction F

[Sal I] [Eco RI]

TCC GTA CTA TCT ATT GTC GAA ATT CGA GCT CGC CCG GGG ATCC

FHV Sal I A pSP 65

FIG. 4B

SEQUENCE LISTING

```
<160> NUMBER OF SEQ ID NOS: 23

<210> SEQ ID NO 1
<211> LENGTH: 2020
<212> TYPE: DNA
<213> ORGANISM: feline herpesvirus 1

<400> SEQUENCE: 1
ggatccatca tcaatagtgc aatacgcaag catataatgg tctgtgctgg gcggcggatc      60
tatataccaa acaacgatgg gcgaccatca acggaaatga cacggtttac tcgccagact     120
```

-continued

| | |
|---|---|
| aaaccatcga attcgagttc caagtccctc ctcgatgtcc ccagatcttc gaattccacc | 180 |
| ccaaccgatg gcgtctctag aagtcagtta accgtaatta acgaagaaac ctaatatatt | 240 |
| tataaacaaa taaatactt ttaaaaatgg atatctggtc atgtgtaatg ttgacgcata | 300 |
| gtgggtggtg acctaagatt atattaaaat gtagaaggtt ttatgcccag ttcacagtat | 360 |
| ctactgtgac ctaccccggg gtggtaataa caatactatc gaatagccaa caatgggact | 420 |
| gcttgttacc atcctcgtga tattattgat tgttacttca tcaagttcta ctattcatca | 480 |
| agtaacgatg acagaaggtg ccgcactttt agtcgatggg gatgggatcg acccacccttt | 540 |
| aaacaaaact tcacattttt tgcgaggttg acatttcta gagactccga aggatgtac | 600 |
| aggagaggtg agtgttctaa agtatgtat agatcgtggg gtatgtccgg atgatatcgt | 660 |
| tataaataag agatgtggtc acaaaatgct tgaaacccca ctagcgttgg cggaatttgg | 720 |
| aatttctaat agttctctca tcagaaccaa agacgtatat ttcgtgaata agaccgtgtt | 780 |
| tccaattctc acacccgaaa aaagtggcct tggtattcag ggggccacta cgaatatatc | 840 |
| cgggatatat accctgcatg agcacggtga taatggatgg agtcatcaat ctacattttt | 900 |
| tgtgaccgta aaggcaaaac atcccggacc atcgttaacc ccagcaccgg ttcacttaat | 960 |
| aacaccacat cgccatgggg cacatttcca cgtaagaaac tatcattcgc atgtctacat | 1020 |
| tccgggagat aagttcttat tagaaatgca cctcaaatca gatatctatg atccagaatt | 1080 |
| ttcagcaaca atagactggt attttatgga gactgatata aaatgcccag tttttagaat | 1140 |
| ttatgaaact tgtatatttc accccatgc cgcatcctgt ctacatccgg aagatccctc | 1200 |
| atgcagttt acatcaccac ttcgagcggt atctttaatt aatagatttt atccaaaatg | 1260 |
| cgatcacaga tatgccgatt ggacatccag atgtatcaac actccaagta taatcatat | 1320 |
| gccatatatc gaacagccgg ccaataacgt ggatctaaag tttatcaatg tacccaccaa | 1380 |
| cgcttctggg ttgtacgtat tcatacttcg ttataatgga catccggaag aatgaccta | 1440 |
| tacactcata tcaacaggag ctaaattttt gaatgtgatt agggatctga cacgcccacg | 1500 |
| tcttggtagt catcaaatag agaccgatat tagcacatct tcgcagtcgc ctaccacgga | 1560 |
| gacaccacga acatacata taacgtgggc gagacgttat ctaaaggtta tcataggaat | 1620 |
| aatttgcgta gctggtatcc ttttgattgt aatctctatc acatgttata ttcgatttcg | 1680 |
| tcatatgcga tataaaccat atgaagtgat caacccattc cctgcggtat ataccagcat | 1740 |
| tcctagtaac gatcccgacg aactctactt tgaacgtatc gcatcgaacg acgaagaatc | 1800 |
| ggcagatgat tcttttgatg aatcagatga ggaggagcca ttgaataatc atcatatttc | 1860 |
| aacaacccaa catactgata ttaatccaga aaaatccgga tctgggtaca gtgtatggtt | 1920 |
| tcgtgataca gaagatacat cacctcagcc cctacacgct cctccagatt acagtcgcgt | 1980 |
| agttaaaaga ttaaagtcta tttaaaatg acccgtcgac | 2020 |

<210> SEQ ID NO 2
<211> LENGTH: 532
<212> TYPE: PRT
<213> ORGANISM: feline herpesvirus 1

<400> SEQUENCE: 2

Met Gly Leu Leu Val Thr Ile Leu Val Ile Leu Ile Val Thr Ser
1               5                   10                  15

Ser Ser Ser Thr Ile His Gln Val Thr Met Thr Glu Gly Ala Ala Leu
                20                  25                  30

Leu Val Asp Gly Asp Gly Ile Asp Pro Pro Leu Asn Lys Thr Ser His

```
              35                  40                  45
Phe Leu Arg Gly Trp Thr Phe Leu Glu Thr Pro Lys Gly Cys Thr Gly
             50                  55                  60

Glu Val Ser Val Leu Lys Val Cys Ile Asp Arg Gly Val Cys Pro Asp
 65                  70                  75                  80

Asp Ile Val Ile Asn Lys Arg Cys Gly His Lys Met Leu Glu Thr Pro
                     85                  90                  95

Leu Ala Leu Ala Glu Phe Gly Ile Ser Asn Ser Ser Leu Ile Arg Thr
                100                 105                 110

Lys Asp Val Tyr Phe Val Asn Lys Thr Val Phe Pro Ile Leu Thr Pro
                115                 120                 125

Glu Lys Ser Gly Leu Gly Ile Gln Gly Ala Thr Thr Asn Ile Ser Gly
            130                 135                 140

Ile Tyr Thr Leu His Glu His Gly Asp Asn Gly Trp Ser His Gln Ser
145                 150                 155                 160

Thr Phe Phe Val Thr Val Lys Ala Lys His Pro Gly Pro Ser Leu Thr
                    165                 170                 175

Pro Ala Pro Val His Leu Ile Thr Pro His Arg His Gly Ala His Phe
                180                 185                 190

His Val Arg Asn Tyr His Ser His Val Tyr Ile Pro Gly Asp Lys Phe
            195                 200                 205

Leu Leu Glu Met His Leu Lys Ser Asp Ile Tyr Asp Pro Glu Phe Ser
        210                 215                 220

Ala Thr Ile Asp Trp Tyr Phe Met Glu Thr Asp Ile Lys Cys Pro Val
225                 230                 235                 240

Phe Arg Ile Tyr Glu Thr Cys Ile Phe His Pro His Ala Ala Ser Cys
                245                 250                 255

Leu His Pro Glu Asp Pro Ser Cys Ser Phe Thr Ser Pro Leu Arg Ala
                260                 265                 270

Val Ser Leu Ile Asn Arg Phe Tyr Pro Lys Cys Asp His Arg Tyr Ala
            275                 280                 285

Asp Trp Thr Ser Arg Cys Ile Asn Thr Pro Ser Ile Asn His Met Pro
        290                 295                 300

Tyr Ile Glu Gln Pro Ala Asn Asn Val Asp Leu Lys Phe Ile Asn Val
305                 310                 315                 320

Pro Thr Asn Ala Ser Gly Leu Tyr Val Phe Ile Leu Arg Tyr Asn Gly
                325                 330                 335

His Pro Glu Glu Trp Thr Tyr Thr Leu Ile Ser Thr Gly Ala Lys Phe
                340                 345                 350

Leu Asn Val Ile Arg Asp Leu Thr Arg Pro Arg Leu Gly Ser His Gln
            355                 360                 365

Ile Glu Thr Asp Ile Ser Thr Ser Ser Gln Ser Pro Thr Thr Glu Thr
        370                 375                 380

Pro Arg Asn Ile His Ile Thr Trp Ala Arg Arg Tyr Leu Lys Val Ile
385                 390                 395                 400

Ile Gly Ile Ile Cys Val Ala Gly Ile Leu Leu Ile Val Ile Ser Ile
                405                 410                 415

Thr Cys Tyr Ile Arg Phe Arg His Met Arg Tyr Lys Pro Tyr Glu Val
            420                 425                 430

Ile Asn Pro Phe Pro Ala Val Tyr Thr Ser Ile Pro Ser Asn Asp Pro
        435                 440                 445

Asp Glu Leu Tyr Phe Glu Arg Ile Ala Ser Asn Asp Glu Glu Ser Ala
450                 455                 460
```

```
Asp Asp Ser Phe Asp Glu Ser Asp Glu Glu Pro Leu Asn Asn His
465                 470                 475                 480

His Ile Ser Thr Thr Gln His Thr Asp Ile Asn Pro Glu Lys Ser Gly
                485                 490                 495

Ser Gly Tyr Ser Val Trp Phe Arg Asp Thr Glu Asp Thr Ser Pro Gln
            500                 505                 510

Pro Leu His Ala Pro Pro Asp Tyr Ser Arg Val Val Lys Arg Leu Lys
            515                 520                 525

Ser Ile Leu Lys
    530

<210> SEQ ID NO 3
<211> LENGTH: 2968
<212> TYPE: DNA
<213> ORGANISM: feline herpesvirus 1

<400> SEQUENCE: 3
```

| | | | | |
|---|---|---|---|---|
| gaattcgatg | ccacaatcgc | ttttatgctg | tcctcaagcg | cgatatatcc tcgacctctg | 60 |
| cgagtggagt | ataccgac | cgactcgagt | gtttattggg | cggctctgta tccgcagagt | 120 |
| ctcttaaaaa | ggctaaggc | gtgtacctag | catgtgaggt | taacttgggt cgtcgccgac | 180 |
| ctgattgtgt | atgtactata | caatttgagg | gagaaggggg | tggtatatgt tttctaattg | 240 |
| agctgaaaac | gtgtcgtttt | tcaaaaaata | tggatacaac | tagtaaagac attcaacgtc | 300 |
| gtgagggttt | gaaacaatta | acagattctg | tgggtttaat | aaccaagatt ctaccaccag | 360 |
| gggggagaa | gctcactcta | atacccatat | tggcatttat | cgcgcagcgc ggtctgagaa | 420 |
| ttttgggagt | tactaattta | cccccgcaga | tgcttacgaa | taacatttct gttctggctg | 480 |
| ctaatattac | caagctcgcc | gaatacaatc | caatcgagag | tggtggtgta atccgctcca | 540 |
| agaaaaaatc | aaaatacca | aggtctgggt | ctggggtcta | taacatacg aaccacgtac | 600 |
| cgatgtcatc | gtgtgtatct | gtgaaggata | aaaaaaacac | tttaactcca ataggaagcg | 660 |
| gcgaaagtaa | ccctttaaaa | tgggtagcat | ctctctcttcc | cgatcactcc gctacgcaac | 720 |
| cacgtgagta | ttaatatgcc | ctatatgtga | tgggtaatga | gtctatatag atcatatatc | 780 |
| aaaaccttat | ttaggatcaa | agagattaat | cactggtatc | atttgttgga gaggagaagt | 840 |
| tgtcgaagac | gggtcatcat | gactggacga | gtcgaatacg | tattcgactc gatgcgaata | 900 |
| actaacatcg | gggatgatct | gattttatcg | gacactagaa | attttattac tcccacattt | 960 |
| ccagtggatt | attggcgtga | gccaaccttt | tatttaaatg | aaaaaactac tcctgaaagt | 1020 |
| ctagatgtcc | gccgaaaggc | tgctgccgcg | gccctggata | atttaaccca tcaaaaacta | 1080 |
| ttgggcgaaa | cggatataga | ggatcgtcta | tatcccttgg | agcaacaggt actaaatgtg | 1140 |
| gctaacgcat | tggcctctct | agaggaggta | gcacgggaag | cggaaacggc ggacgctgag | 1200 |
| atggataagg | atactagacc | tctccagtct | aatggtggaa | gcagatcgga tgagacacct | 1260 |
| ggagggcttg | aggttcagat | taccaaaaat | gacactccat | tggcatatga acaaaaccta | 1320 |
| gccatagatt | ttttaacgat | ggtatattta | gggcgtgccg | cgggatcaaa tggtatatca | 1380 |
| tttggttcat | ggtatagagc | gttacaagat | cgtcttatca | cagatcgtcc gttaaccacc | 1440 |
| agaagtatag | attatcgaga | tgggcgaatg | tctaaaactt | ccatgacagc aacaataatg | 1500 |
| tctctccaat | cctgtgcccg | actctatatc | gggaatagag | cctactcggc ttttgaatgt | 1560 |
| gcagttttat | gtcttcatct | tttacatcgg | gaactcgata | agggaatcat gacgcaccca | 1620 |
| ccgactacat | tttccgatct | aatagagcac | ctaccgacat | cattggatat tattgctaac | 1680 |

-continued

```
accctaggta ctatgccgtc tggtagagta atttatatat ataatataga taaactacct    1740
agacatcaat ttcaggcgcc taatggtgga cggtatgaac atcatgccct tgaagaccat    1800
agcgtattaa atctacttct ccaatttaag gttttacctc cgattcctgg acatattaaa    1860
ggtggtcccc cggctatagc catagatata gaccagactg ctttcgtaga cccggttaat    1920
agagccgcgg cagctttcct agggagggca cataatctat ttctcacgga ggatcagacg    1980
cttctcagag ctactataaa cactataacc tcactattac tactccgacg cttactatgg    2040
aatggaaaca tctatacgga taaattacgt aataatttcc agcttggaac actcatsccc    2100
cagacagcct ctatacagat gctgggtaca ttgactcgcg gggcaaccgg ggggggatttg    2160
ggagcaccac tcaccataaa aagcgagagt cacaatctag agtttttatg ttctagatat    2220
atattaccga tctatacatc tatgccagat gtcgagatca cgcaattatt tccgggtctt    2280
acagcgctat gtttagatgc gcaagccctc atagcacaaa cccgcaccgc gaggcgcgtg    2340
gtgcaagtga aaactggacg tttgcaggac aacttaattc ggttggttgg tctcgaactc    2400
gaaaatagac gccggacagg aacagtaccc ataggtgagg tgatcacggc acacgacgct    2460
atatctcttc aaactgaaca tggcttgggt cttctcatgc aacaaccacg acttagagcc    2520
tctcttgagg aaaatcatcg cttatggcaa tttaacattg gcagtgatta cgatctaata    2580
tactttctgt gtttggggta tatacctcaa ttcacagcat ctatataact gaatgttttt    2640
gctaagtaga tcatatacga aataaacatt acatattaaa tataacacac ctggtgcgtg    2700
tgggtctttt tattttcaac cggctctcca gtaggaagca ccagtttctt cacatgcaat    2760
ggatacacac gatattatcg aggataccac atccgatctc catatctacg tggctggtta    2820
tctagccctc tatgatatgg gagatggcgg ggaattgact ttaactcgtg atgtggtgcg    2880
tgcagcattg cccccagcat caccactaca gattaatata gatcataatc gtaaatgtgt    2940
catcggttcc gtactatcta ttgtcgac                                       2968
```

<210> SEQ ID NO 4
<211> LENGTH: 240
<212> TYPE: PRT
<213> ORGANISM: feline herpesvirus 1

<400> SEQUENCE: 4

```
Ile Arg Cys His Asn Arg Phe Tyr Ala Val Leu Lys Arg Asp Ile Ser
1               5                   10                  15

Ser Thr Ser Ala Ser Gly Val Tyr Thr Asp Arg Leu Glu Cys Leu Leu
            20                  25                  30

Gly Gly Ser Val Ser Ala Glu Ser Leu Lys Lys Ala Lys Gly Val Tyr
        35                  40                  45

Leu Ala Asn Leu Gly Arg Arg Pro Asp Cys Val Cys Thr Ile Gln
    50                  55                  60

Phe Glu Gly Glu Gly Gly Ile Cys Phe Leu Ile Glu Leu Lys Thr
65                  70                  75                  80

Cys Arg Phe Ser Lys Asn Met Asp Thr Thr Ser Lys Asp Ile Gln Arg
                85                  90                  95

Arg Glu Gly Leu Lys Gln Leu Thr Asp Ser Val Gly Leu Ile Thr Lys
            100                 105                 110

Ile Leu Pro Pro Gly Gly Glu Lys Leu Thr Leu Ile Pro Ile Leu Ala
        115                 120                 125

Phe Ile Ala Gln Arg Gly Leu Arg Ile Leu Gly Val Thr Asn Leu Pro
    130                 135                 140
```

```
Pro Gln Met Leu Thr Asn Asn Ile Ser Val Leu Ala Ala Asn Ile Thr
145                 150                 155                 160

Lys Leu Ala Glu Tyr Asn Pro Ile Glu Ser Gly Gly Val Ile Arg Ser
            165                 170                 175

Lys Lys Lys Ser Lys Tyr Pro Arg Ser Gly Ser Gly Val Tyr Lys His
            180                 185                 190

Thr Asn His Val Pro Met Ser Ser Cys Val Ser Val Lys Asp Lys Lys
            195                 200                 205

Asn Thr Leu Thr Pro Ile Gly Ser Gly Glu Ser Asn Pro Leu Lys Trp
        210                 215                 220

Val Ala Ser Leu Phe Pro Asp His Ser Ala Thr Gln Pro Arg Glu Tyr
225                 230                 235                 240

<210> SEQ ID NO 5
<211> LENGTH: 589
<212> TYPE: PRT
<213> ORGANISM: feline herpesvirus 1

<400> SEQUENCE: 5

Met Thr Gly Arg Val Glu Tyr Val Phe Asp Ser Met Arg Ile Thr Asn
1               5                   10                  15

Ile Gly Asp Asp Leu Ile Leu Ser Asp Thr Arg Asn Phe Ile Thr Pro
            20                  25                  30

Thr Phe Pro Val Asp Tyr Trp Arg Glu Pro Thr Phe Tyr Leu Asn Glu
        35                  40                  45

Lys Thr Thr Pro Glu Ser Leu Asp Val Arg Arg Lys Ala Ala Ala Ala
    50                  55                  60

Ala Leu Asp Asn Leu Thr His Gln Lys Leu Leu Gly Glu Thr Asp Ile
65                  70                  75                  80

Glu Asp Arg Leu Tyr Pro Leu Glu Gln Gln Val Leu Asn Val Ala Asn
                85                  90                  95

Ala Leu Ala Ser Leu Glu Glu Val Ala Arg Glu Ala Glu Thr Ala Asp
            100                 105                 110

Ala Glu Met Asp Lys Asp Thr Arg Pro Leu Gln Ser Asn Gly Gly Ser
        115                 120                 125

Arg Ser Asp Glu Thr Pro Gly Gly Leu Glu Val Gln Ile Thr Lys Asn
130                 135                 140

Asp Thr Pro Leu Ala Tyr Glu Thr Asn Leu Ala Ile Asp Phe Leu Thr
145                 150                 155                 160

Met Val Tyr Leu Gly Arg Ala Ala Gly Ser Asn Gly Ile Ser Phe Gly
                165                 170                 175

Ser Trp Tyr Arg Ala Leu Gln Asp Arg Leu Ile Thr Asp Arg Pro Leu
            180                 185                 190

Thr Thr Arg Ser Ile Asp Tyr Arg Asp Gly Arg Met Ser Lys Thr Ser
        195                 200                 205

Met Thr Ala Thr Ile Met Ser Leu Gln Ser Cys Ala Arg Leu Tyr Ile
    210                 215                 220

Gly Asn Arg Ala Tyr Ser Ala Phe Glu Cys Ala Val Leu Cys Leu His
225                 230                 235                 240

Leu Leu His Arg Glu Leu Asp Lys Gly Ile Met Thr His Pro Pro Thr
                245                 250                 255

Thr Phe Ser Asp Leu Ile Glu His Leu Pro Thr Ser Leu Asp Ile Ile
            260                 265                 270

Ala Asn Thr Leu Gly Thr Met Pro Ser Gly Arg Val Ile Tyr Ile Tyr
```

```
                275                 280                 285
Asn Ile Asp Lys Leu Pro Arg His Gln Phe Gln Ala Pro Asn Gly Gly
            290                 295                 300

Arg Tyr Glu His His Ala Leu Glu Asp His Ser Val Leu Asn Leu Leu
305                 310                 315                 320

Leu Gln Phe Lys Val Leu Pro Pro Ile Pro Gly His Ile Lys Gly Gly
                325                 330                 335

Pro Pro Ala Ile Ala Ile Asp Ile Asp Gln Thr Ala Phe Val Asp Pro
            340                 345                 350

Val Asn Arg Ala Ala Ala Phe Leu Gly Arg Ala His Asn Leu Phe
            355                 360                 365

Leu Thr Glu Asp Gln Thr Leu Leu Arg Ala Thr Ile Asn Thr Ile Thr
    370                 375                 380

Ser Leu Leu Leu Leu Arg Arg Leu Leu Trp Asn Gly Asn Ile Tyr Thr
385                 390                 395                 400

Asp Lys Leu Arg Asn Asn Phe Gln Leu Gly Thr Leu Ile Pro Gln Thr
                405                 410                 415

Ala Ser Ile Gln Met Leu Gly Thr Leu Thr Arg Gly Ala Thr Gly Gly
            420                 425                 430

Asp Leu Gly Ala Pro Leu Thr Ile Lys Ser Glu Ser His Asn Leu Glu
            435                 440                 445

Phe Leu Cys Ser Arg Tyr Ile Leu Pro Ile Tyr Thr Ser Met Pro Asp
    450                 455                 460

Val Glu Ile Thr Gln Leu Phe Pro Gly Leu Thr Ala Leu Cys Leu Asp
465                 470                 475                 480

Ala Gln Ala Leu Ile Ala Gln Thr Arg Thr Ala Arg Arg Val Val Gln
                485                 490                 495

Val Lys Thr Gly Arg Leu Gln Asp Asn Leu Ile Arg Leu Val Gly Leu
            500                 505                 510

Glu Leu Glu Asn Arg Arg Thr Gly Thr Val Pro Ile Gly Glu Val
            515                 520                 525

Ile Thr Ala His Asp Ala Ile Ser Leu Gln Thr Glu His Gly Leu Gly
    530                 535                 540

Leu Leu Met Gln Gln Pro Arg Leu Arg Ala Ser Leu Glu Glu Asn His
545                 550                 555                 560

Arg Leu Trp Gln Phe Asn Ile Gly Ser Asp Tyr Asp Leu Ile Tyr Phe
                565                 570                 575

Leu Cys Leu Gly Tyr Ile Pro Gln Phe Thr Ala Ser Ile
            580                 585

<210> SEQ ID NO 6
<211> LENGTH: 69
<212> TYPE: PRT
<213> ORGANISM: feline herpesvirus 1

<400> SEQUENCE: 6

Met Asp Thr His Asp Ile Ile Glu Asp Thr Thr Ser Asp Leu His Ile
1               5                   10                  15

Tyr Val Ala Gly Tyr Leu Ala Leu Tyr Asp Met Gly Asp Gly Gly Glu
            20                  25                  30

Leu Thr Leu Thr Arg Asp Val Val Arg Ala Ala Leu Pro Pro Ala Ser
        35                  40                  45

Pro Leu Gln Ile Asn Ile Asp His Asn Arg Lys Cys Val Ile Gly Ser
    50                  55                  60
```

Val Leu Ser Ile Val
65

<210> SEQ ID NO 7
<211> LENGTH: 1730
<212> TYPE: DNA
<213> ORGANISM: feline herpesvirus 1

<400> SEQUENCE: 7

| gtcgacgacc | ggccatcgcg | aagacaacgc | ttctcgggcg | atgaatgtga | ataccaatgt | 60 |
| ccactaatcc | cgggtctttt | ataggtgtc | cggcattcga | catgatgctg | aatcgtttcc | 120 |
| ggggaaaacc | cccaaatttc | cgagacgttt | tagtgtggca | tgcgtcgaag | ttcgctgctt | 180 |
| accatgcgta | gacacatccg | gtaggcgtaa | caaatcatag | ccacacccac | ggcaatcaag | 240 |
| gacatgtaaa | ataaaacagc | ggatgcagtg | ggggtgtttg | atattcacac | cccttgccga | 300 |
| acacgaagcg | ctccaaaatt | gctttagccg | ctccatactc | tcaaaatctt | ccgcgtttgc | 360 |
| ggggcatctg | aatcgctgta | gtagaagaat | ggcgaccaat | aggataacca | gcactgatgt | 420 |
| tacggataaa | cgatccatct | ccgttttggt | agaaaagact | tcagaggcgt | ggagtttatt | 480 |
| ggtcagtgag | aatgctctgt | tggtgacaaa | taatcaacca | atcgagcttg | ggttgatgag | 540 |
| tagagagccg | gataatgcgg | acatctttta | taccagaccg | gtagatattg | gcttagatt | 600 |
| agccacgcct | gatggatatg | caattttaat | tacgcaaacg | tgctcctccc | aagatcccag | 660 |
| tcaagcagtg | tcaatcatca | atggggttat | cgattctggg | tatcgcggaa | ttctcaaagc | 720 |
| gctaatctac | cacagaccgt | gtatcgagac | tattaaggag | tatggtctaa | agttacaact | 780 |
| acctctactc | aagcttagta | aagctacgat | tacattagca | ccatgtcctg | ctacgattag | 840 |
| gcataaacaa | ggggtcccaa | tgggtgctcg | actgtgtgat | ttctatgaaa | ttttttaaaca | 900 |
| aaaacgggac | gaagatgctg | gttatgatat | atccgcacct | gaaacgttcc | agatttatcc | 960 |
| gggatttaat | cactatgtag | agatcccagt | agttcacctt | ccgggtgaca | accccccat | 1020 |
| agcatgtatc | tttgggaggt | cttctcttaa | cgtgagtggt | atcgtagttc | tccctactgt | 1080 |
| atggaaacct | gagacaaaat | gtgggttctt | cataaaaaat | atgcgtcgcg | atccagtaat | 1140 |
| cattagagct | gggcaaagga | ttgcccagtt | attacttctg | gaagaattac | ctatggaatg | 1200 |
| gctacctacg | gaaacgaata | atcacgatcc | atttccagaa | accccagaac | ctgcacctgg | 1260 |
| aacaatcatg | gctcacgcgg | atttatggac | ctttactgaa | aacttcatcg | tgatgcccca | 1320 |
| tcgagccttc | gggggataa | aggatttggg | tcaaccgggg | tataataaaa | taaacgatat | 1380 |
| gataaataac | ataacaacga | atctgttttt | tattccatag | tcaattctgt | ttgtcgatgt | 1440 |
| gatttgcgct | tggatttttt | agtatgtctt | atagaatctc | cattatcaaa | gatatggtcg | 1500 |
| ttaaccagaa | ccggttcacg | ggctacgacg | tttggagtta | tgtccatagt | agtaacagat | 1560 |
| gtgacattcg | ggtgatttga | tattttgcac | tcctccgatg | cggatggttg | attagtaact | 1620 |
| agatgtctgt | tccccgagct | tgcagcaccg | ataccaaaag | tcttctctaa | tacagctaca | 1680 |
| tcggccatca | caatgttatt | ttcggaactc | atgcgtatgg | cttggtcgac | | 1730 |

<210> SEQ ID NO 8
<211> LENGTH: 384
<212> TYPE: PRT
<213> ORGANISM: feline herpesvirus 1

<400> SEQUENCE: 8

Met Gln Trp Gly Cys Leu Ile Phe Thr Pro Leu Ala Glu His Glu Ala
1               5                   10                  15

-continued

```
Leu Gln Asn Cys Phe Ser Arg Ser Ile Leu Ser Lys Ser Ser Ala Phe
             20                  25                  30

Ala Gly His Leu Asn Arg Cys Ser Arg Arg Met Ala Thr Asn Arg Ile
         35                  40                  45

Thr Ser Thr Asp Val Thr Asp Lys Arg Ser Ile Ser Val Leu Val Glu
 50                  55                  60

Lys Thr Ser Glu Ala Trp Ser Leu Leu Val Ser Glu Asn Ala Leu Leu
 65                  70                  75                  80

Val Thr Asn Asn Gln Pro Ile Glu Leu Gly Leu Met Ser Arg Glu Pro
                 85                  90                  95

Asp Asn Ala Asp Ile Phe Tyr Thr Arg Pro Val Asp Ile Gly Leu Arg
             100                 105                 110

Leu Ala Thr Pro Asp Gly Tyr Ala Ile Leu Ile Thr Gln Thr Cys Ser
         115                 120                 125

Ser Gln Asp Pro Ser Gln Ala Val Ser Ile Ile Asn Gly Val Ile Asp
 130                 135                 140

Ser Gly Tyr Arg Gly Ile Leu Lys Ala Leu Ile Tyr His Arg Pro Cys
145                 150                 155                 160

Ile Glu Thr Ile Lys Glu Tyr Gly Leu Lys Leu Gln Leu Pro Leu Leu
                 165                 170                 175

Lys Leu Ser Lys Ala Thr Ile Thr Leu Ala Pro Cys Pro Ala Thr Ile
             180                 185                 190

Arg His Lys Gln Gly Val Pro Met Gly Ala Arg Leu Cys Asp Phe Tyr
         195                 200                 205

Glu Ile Phe Lys Gln Lys Arg Asp Glu Asp Ala Gly Tyr Asp Ile Ser
 210                 215                 220

Ala Pro Glu Thr Phe Gln Ile Tyr Pro Gly Phe Asn His Tyr Val Glu
225                 230                 235                 240

Ile Pro Val Val His Leu Pro Gly Asp Asn Pro Ile Ala Cys Ile
                 245                 250                 255

Phe Gly Arg Ser Ser Leu Asn Val Ser Gly Ile Val Val Leu Pro Thr
             260                 265                 270

Val Trp Lys Pro Glu Thr Lys Cys Gly Phe Phe Ile Lys Asn Met Arg
         275                 280                 285

Arg Asp Pro Val Ile Ile Arg Ala Gly Gln Arg Ile Ala Gln Leu Leu
 290                 295                 300

Leu Leu Glu Glu Leu Pro Met Glu Trp Leu Pro Thr Glu Thr Asn Asn
305                 310                 315                 320

His Asp Pro Phe Pro Glu Thr Pro Glu Pro Ala Pro Gly Thr Ile Met
                 325                 330                 335

Ala His Ala Asp Leu Trp Thr Phe Thr Glu Asn Phe Ile Val Met Pro
             340                 345                 350

His Arg Ala Phe Gly Gly Ile Lys Asp Leu Gly Gln Pro Gly Tyr Asn
         355                 360                 365

Lys Ile Asn Asp Met Ile Asn Asn Ile Thr Thr Lys Ser Val Phe Ile
 370                 375                 380
```

<210> SEQ ID NO 9
<211> LENGTH: 4881
<212> TYPE: DNA
<213> ORGANISM: feline herpesvirus 1

<400> SEQUENCE: 9
ttcgactcta caatcttgta gattttgggt tgtaggtggt gtgttgtcga ttggaggtcc    60

-continued

```
accaacagtg acggtctcta ccggccatcc ccattcccg agaatcgtca aataggtct      120 gatatcgtcc atctacgtta ggttggagaa gcaccataaa cgacgtagtt ttgctgtggg     180
ttttaagtat accgaaggcc tccttatcgc gtaagttgtt ttcgtcatat acttcactca     240
ttcaacactc caatcgatgg ctcccttacc cctctttaca agaaactcat ttgccattct     300
aaaatgcgta cactcgctaa atgggatacg tgacagtgga gatggatggg tatatgtcag     360
tatcaaatgc cgatgtggat ctgggttaca agcttttttgg gcgtgggatc cccataacat    420
aaataccagc ccatcagaaa tcgatgccag atgatctaat atagccttaa ctaattttttc    480 ccaaccaatc attctatgag atccaggact cccccgtcta actgtgagtg tagtgttaat     540
taataatact cctctttcca cccatttaag aagattacca tgcttcccga ttcggatatc     600
ggggtaattc ttccgtagtg ccgcgtagat gtttctgaga ctcggaggaa tggttacgtt     660
ctcatgaacg ctaaacgcca ggccattggc ttgaccgggt ccgtggtatg atcttgtcc      720 caagatgact actttaatgt ccatgggttg tatcgcacgt gtccatgaaa atatatcttg     780
tattttaggt aggacctctt catagcgtag acgacgttcg tattccagta aaatgcgttg     840
ggtatacggt ttcttaaatt caggttcgag aatagatgcc catgaatgtg atatattaaa    900
ctttcgttgg atagtcatcc acgaaatcgg tttctctata ttggaaacca cttgtacatc    960
tggatctaaa attactccag atgggagacc ggtgggtctc aattttttttc ttggtggctc   1020 tgtagatgta gtatctgatg gagcattggt agtgcaatag gtatggtcga gagctacaac   1080
agctgaatta tgattcacaa gctcattcat agttgacata gatataaggt tagtatatct   1140
cagcgatata tactaacctt ttttgtttgt aggttaagga agctttatac tatcttgtag   1200
agatggagag tcacgtggag gcggtggaag agtatctgca tccggggcaa gttgatctcg   1260
tcggaaagct gtgtccagaa catcagtgaa tctggatttt aagtgtattg ggacggacat   1320
ccgtctgaca tcttcagcca atccctgtag tgcaacaaag ggattaaccc aatatgctcg   1380
tttatcccct ttaaaccaca gtattacctc cggtgggtta caatctgctc gcacgataat   1440
tccagccaaa tcttctttga tattttcatc acctagtcca tataattttt tttctactcg   1500
gtgatcacgg catggtccta aaagaattac atcaatccca tcgtattgga cttgctcctc   1560
cgaggcacca aaatctggaa tataaatctt caagagtaat aaaacgaaga cccacatcgt   1620
ggaaagacca gcggtcgata tacctgtgaa atcacacaa cctaatatgt agaacggtct    1680
caaaaaccaa ctaacccaac ccaatagtga gtgccattta tatagtatgg tatacaccct   1740
gaaatacagt caaatgtcat atacatttat gtgattcaaa tatttattat gcccgtctat   1800
tagacagttt acagtattcg attatgtagt actcctaata tccggtagat agcgtatttg   1860
tctgcaaaac attcttctgt agtggactct ggtaataact cctatcgatc tataaacaaa   1920
aagccatttg tttaagccat taaggggggaa cttaagattc tggaaaaagc tattccagcc   1980
attaaatggg aacacagagt ttggaaacag cacactacat cctttttagta agaattcatg   2040 aataaaatat aattccacat ttattatata ggtccgtata gctgcgtgcg ggtgggagca   2100
tctgaggcta ttcatcccg gggcaagatg tacgaggaca tcgtgataaa gataagtaac    2160
aatttcctac cggggggttta tatccagaat attaaatgct gggggcccac caatctcggc   2220
ggtctttatt ttgtataaac tgacaacact gagtttcatg tgtattacta tctttattaa   2280
tgatatatcc aacaataatt acattgttct actacaatct ggtattcggt atatgtacga   2340
tcggcccaga taccctccta cgacccctgc gggttgtctg taaccgtgta tgagaaatcg   2400
```

```
cagtggtcga agagtctcgt tgagtcatat ttgacgtcga tggggttgat actaaattaa    2460
aggtttctgg gctcccctc aatctagcag acctccgctc gttccatcga dacggggtc      2520
gtttgcgctt tctatcggtt ggggttacgc ttatgggagt attatgacta ccagaatcgg    2580
tgttgggagg tccatcggca tcatgaacac ctctgatatc atcctcattt ttttgatacc    2640
tggatgaaac tgtagtattt actataggat cggctctgcc gtcatcatag gaaactgcag    2700
tattttctgt agtattggtt ctgtcgttat ttgcgccatc tagagctatt acagtagtac    2760
tgttttcatt agaactttct gtgtcatgag ccagagtaag gtctaaaggt tccatattgg    2820
tctccggata gttctgttgt atcgattcag ccggagccgc gaaattggta gccgatgacc    2880
cgtgtggaag tgtagataac tcaggctgtg tatttagtga atgacgtgtc tcatcatcta    2940
tccctgtagt gataccaaca gataagtctg tgccaattgt ggtctctgta tcgtcagaat    3000
catcggtatc atcatatgca gtgtcctcgg ggtctgtgag atctgctgtg gcagagactag   3060
acgattcatc gtcggaggag gtatcgtctt ctgtatcatc taggaattgg accccggttg    3120
aaacgcgtaa agtacgggcc gtagaaggaa atacgcactg tgatgcttcg gcgagcaacc    3180
gtatcacgaa gagatccgtc tgtgtgtgga gcagggtct gagaaggcga gtaagcgcag     3240
cgctattgaa tgcatgctcg cacagctcat ccataacaat accacacatg acactggctg    3300
ttgtctcatc gttgtaataa ttcaaaagcc agctgttcat ccacgttact agagggcgca    3360
gatgtggggc tccggcaccc ccgtctgggg tcagggcac aaatcccagt cctgtagatg      3420
tagaatcccg tggtcttgtt gaagttggat tacctgcccc atcgctgggt cgtccagagg    3480
tatcaaccgt tgttgaattt tcaagacgaa cactgttcag agatatatta gcccatcgtc    3540
gggcttcagt ccatataaac ggatcccaat cgagatactc ctcctcctct ctatgtgggc    3600
tatatagttt cgtttcttca aagattttat cgtcctctat agagtggatg agcgatgtca    3660
cactagtttt acagagggga catttgttat ttaatcctac ccacctactg agacaggaat    3720
agcaaaattt atgcaaacat ggcatggtga agttaaaatc attcatggga tcaaggcata    3780
ttggacagtg gtctcccata tcagccatgt cgaggtcctc tacccagacc aaaaagagtt    3840
atgtcaggtc cttacaaatc aatcagaccc aagtcggact cacgacttta atatatacccc   3900
ataacaggaa gtgagctctt gggatatata tgttgtcagt gttcatcaaa attctcattc    3960
ggtagacaca tgtgataggg tttcgtttct agaaatacct cccatactaa aatgtaatgt    4020
tctaatatat cgttctgtga tctatgtaaa taatagcagc gcatcgagta tctgctaggc    4080
gggcttttctt ctggatctta tccatcggaa atccacaccg gcccaaagct tcaagttact   4140
ttcactttca gtgatttata aactacttag aatcccataa gacctcttac ttgtattgat    4200
tttatgatat cttggggctt tcccctgact aaaaattcac cgggtcttgt ttcatgttac    4260
cacagtccaa acatttaat ataatagtta tttttatctc acatgcaaaa aatataatag      4320
gtggataagt atcaatgttc ttttccaaaa aaatcacatt cccattcgta tctcggaatg    4380
gctacctgca tgtctggcct tagtactaaa tcgcatgttt ctatacgatg tatctgatttt   4440
gcatgctcgt gtatcatgta tcggtcatgg ggatcccact acgttccact aaaaaccatt    4500
tctagacatc ccgaagttcg gatggaatgt tggttacttc ccccactccg gccgccgcgg    4560
gagatctcgg ccccctagc cacttttccg agggggtcca aaaaggggggc gggtcttt      4620
tttgggggc gtggctaggg ggcctcccct tccttattag gccctccccc ttccttatta     4680
ggccctccc cttccttatt aggcccctcc ccttcctat taggccctc cccttcctta        4740
ttaggccct ccccttcctt attaggccc tcccttcct tattaggccc ctccccttcc        4800
```

```
ttattaggcc ctcccccttc cttattaagc ccctcccctt ccttattagg ccccctcccct    4860 tccttattaa gcccctcccc t                                               4881
```

<210> SEQ ID NO 10
<211> LENGTH: 293
<212> TYPE: PRT
<213> ORGANISM: feline herpesvirus 1

<400> SEQUENCE: 10

Met Ser Thr Met Asn Glu Leu Val Asn His Asn Ser Ala Val Val Ala
1               5                   10                  15

Leu Asp His Thr Tyr Cys Thr Thr Asn Ala Pro Ser Asp Thr Thr Ser
            20                  25                  30

Thr Glu Pro Pro Arg Lys Lys Leu Arg Pro Thr Gly Leu Pro Ser Gly
        35                  40                  45

Val Ile Leu Asp Pro Asp Val Gln Val Ser Asn Ile Glu Lys Pro
    50                  55                  60

Ile Ser Trp Met Thr Ile Gln Arg Lys Phe Asn Ile Ser His Ser Trp
65                  70                  75                  80

Ala Ser Ile Leu Glu Pro Glu Phe Lys Lys Pro Tyr Thr Gln Arg Ile
                85                  90                  95

Leu Leu Glu Tyr Glu Arg Arg Leu Arg Tyr Glu Val Leu Pro Lys
            100                 105                 110

Ile Gln Asp Ile Phe Ser Trp Thr Arg Ala Ile Gln Pro Met Asp Ile
        115                 120                 125

Lys Val Val Ile Leu Gly Gln Asp Pro Tyr His Gly Pro Gly Gln Ala
    130                 135                 140

Asn Gly Leu Ala Phe Ser Val His Glu Asn Val Thr Ile Pro Pro Ser
145                 150                 155                 160

Leu Arg Asn Ile Tyr Ala Ala Leu Arg Lys Asn Tyr Pro Asp Ile Arg
                165                 170                 175

Ile Gly Lys His Gly Asn Leu Leu Lys Trp Val Glu Arg Gly Val Leu
            180                 185                 190

Leu Ile Asn Thr Thr Leu Thr Val Arg Arg Gly Ser Pro Gly Ser His
        195                 200                 205

Arg Met Ile Gly Trp Glu Lys Leu Val Lys Ala Ile Leu Asp His Leu
    210                 215                 220

Ala Ser Ile Ser Asp Gly Leu Val Phe Met Leu Trp Gly Ser His Ala
225                 230                 235                 240

Gln Lys Ala Cys Asn Pro Asp Pro His Arg His Leu Ile Leu Thr Tyr
                245                 250                 255

Thr His Pro Ser Pro Leu Ser Arg Ile Pro Phe Ser Glu Cys Thr His
            260                 265                 270

Phe Arg Met Ala Asn Glu Phe Leu Val Lys Arg Gly Lys Gly Ala Ile
        275                 280                 285

Asp Trp Ser Val Glu
    290

<210> SEQ ID NO 11
<211> LENGTH: 147
<212> TYPE: PRT
<213> ORGANISM: feline herpesvirus 1

<400> SEQUENCE: 11

Met Trp Val Phe Val Leu Leu Leu Leu Lys Ile Tyr Ile Pro Asp Phe

-continued

```
1               5                   10                  15

Gly Ala Ser Glu Glu Gln Val Gln Tyr Asp Gly Ile Asp Val Ile Leu
                20                  25                  30

Leu Gly Pro Cys Arg Asp His Arg Val Glu Lys Lys Leu Tyr Gly Leu
                35                  40                  45

Gly Asp Glu Asn Ile Lys Glu Asp Leu Ala Gly Ile Ile Val Arg Ala
            50                  55                  60

Asp Cys Asn Pro Pro Glu Val Ile Leu Trp Phe Lys Gly Asp Lys Arg
65                  70                  75                  80

Ala Tyr Trp Val Asn Pro Phe Val Ala Leu Gln Gly Leu Ala Glu Asp
                    85                  90                  95

Val Arg Arg Met Ser Val Pro Ile His Leu Lys Ser Arg Phe Thr Asp
                100                 105                 110

Val Leu Asp Thr Ala Phe Arg Arg Asp Gln Leu Ala Pro Asp Ala Asp
            115                 120                 125

Thr Leu Pro Pro Pro Arg Asp Ser Pro Ser Leu Gln Asp Ser Ile
            130                 135                 140

Lys Leu Pro
145

<210> SEQ ID NO 12
<211> LENGTH: 498
<212> TYPE: PRT
<213> ORGANISM: feline herpesvirus 1

<400> SEQUENCE: 12

Met Ala Asp Met Gly Asp His Cys Pro Ile Cys Leu Asp Pro Met Asn
1               5                   10                  15

Asp Leu Thr Phe Thr Met Pro Cys Leu His Lys Phe Cys Tyr Ser Cys
                20                  25                  30

Leu Ser Arg Trp Val Gly Leu Asn Lys Cys Pro Leu Cys Lys Thr
                35                  40                  45

Ser Val Thr Ser Leu Ile His Ser Ile Glu Asp Asp Lys Ile Phe Glu
            50                  55                  60

Glu Thr Lys Leu Tyr Ser Pro His Arg Glu Glu Glu Tyr Leu Asp
65                  70                  75                  80

Trp Asp Pro Phe Ile Trp Thr Glu Ala Arg Arg Trp Ala Asn Ile Ser
                    85                  90                  95

Leu Asn Ser Val Arg Leu Glu Asn Ser Thr Thr Val Asp Thr Ser Gly
                100                 105                 110

Arg Pro Ser Asp Gly Ala Gly Asn Pro Thr Ser Thr Arg Pro Arg Asp
            115                 120                 125

Ser Thr Ser Thr Gly Leu Gly Phe Val Pro Leu Thr Pro Asp Gly Gly
130                 135                 140

Ala Gly Ala Pro His Leu Arg Pro Leu Val Thr Trp Met Asn Ser Trp
145                 150                 155                 160

Leu Leu Asn Tyr Tyr Asn Asp Glu Thr Thr Ala Ser Val Met Cys Gly
                165                 170                 175

Ile Val Met Asp Glu Leu Cys Glu His Ala Phe Asn Ser Ala Ala Leu
                180                 185                 190

Thr Arg Leu Leu Arg Pro Leu Leu His Thr Gln Thr Asp Leu Phe Val
            195                 200                 205

Ile Arg Leu Leu Ala Glu Ala Ser Gln Cys Val Phe Pro Ser Thr Ala
        210                 215                 220
```

-continued

```
Arg Thr Leu Arg Val Ser Thr Gly Val Gln Phe Leu Asp Asp Thr Glu
225                 230                 235                 240

Asp Asp Thr Ser Ser Asp Asp Glu Ser Ser Leu Ala Thr Ala Asp
            245                 250                 255

Leu Thr Asp Pro Glu Asp Thr Ala Tyr Asp Asp Thr Asp Asp Ser Asp
            260                 265                 270

Asp Thr Glu Thr Thr Ile Gly Thr Asp Leu Ser Val Gly Ile Thr Thr
            275                 280                 285

Gly Ile Asp Asp Glu Thr Arg His Ser Leu Asn Thr Gln Pro Glu Leu
            290                 295                 300

Ser Thr Leu Pro His Gly Ser Ser Ala Thr Asn Phe Ala Ala Pro Ala
305                 310                 315                 320

Glu Ser Ile Gln Gln Asn Tyr Pro Glu Thr Asn Met Glu Pro Leu Asp
                325                 330                 335

Leu Thr Leu Ala His Asp Thr Glu Ser Ser Asn Glu Asn Ser Thr Thr
            340                 345                 350

Val Ile Ala Leu Asp Gly Ala Asn Asn Asp Arg Thr Asn Thr Thr Glu
            355                 360                 365

Asn Thr Ala Val Ser Tyr Asp Asp Gly Arg Ala Asp Pro Ile Val Asn
370                 375                 380

Thr Thr Val Ser Ser Arg Tyr Gln Lys Asn Glu Asp Asp Ile Arg Gly
385                 390                 395                 400

Val His Asp Ala Asp Gly Pro Pro Asn Thr Asp Ser Gly Ser His Asn
            405                 410                 415

Thr Pro Ile Ser Val Thr Pro Thr Asp Arg Lys Arg Lys Arg Pro Pro
            420                 425                 430

Ser Arg Trp Asn Glu Arg Arg Ser Ala Arg Leu Arg Gly Ser Pro Glu
            435                 440                 445

Thr Phe Asn Leu Val Ser Thr Pro Ser Thr Ser Asn Met Thr Gln Arg
            450                 455                 460

Asp Ser Ser Thr Thr Ala Ile Ser His Thr Arg Leu Gln Thr Arg
465                 470                 475                 480

Arg Gly Arg Arg Arg Val Ser Gly Pro Ile Val His Ile Pro Asn Thr
                485                 490                 495

Arg Leu

<210> SEQ ID NO 13
<211> LENGTH: 33
<212> TYPE: DNA
<213> ORGANISM: feline herpesvirus

<400> SEQUENCE: 13
gaatacacgg aattaattcg atgccacaat cgc                              33

<210> SEQ ID NO 14
<211> LENGTH: 26
<212> TYPE: DNA
<213> ORGANISM: feline herpesvirus

<400> SEQUENCE: 14
aaaggctgct gcctcgacgt ctgggg                                      26

<210> SEQ ID NO 15
<211> LENGTH: 34
<212> TYPE: DNA
<213> ORGANISM: feline herpesvirus
```

-continued

```
<400> SEQUENCE: 15
gcctggtgtc cgtcgaggca gctttcctag ggag                              34

<210> SEQ ID NO 16
<211> LENGTH: 43
<212> TYPE: DNA
<213> ORGANISM: feline herpesvirus

<400> SEQUENCE: 16
tccgtactat ctattgtcga aattcgagct cgcccgggga tcc                    43

<210> SEQ ID NO 17
<211> LENGTH: 33
<212> TYPE: DNA
<213> ORGANISM: feline herpesvirus

<400> SEQUENCE: 17
gaatacacgg aattaattcg atgccacaat cgc                               33

<210> SEQ ID NO 18
<211> LENGTH: 36
<212> TYPE: DNA
<213> ORGANISM: feline herpesvirus

<400> SEQUENCE: 18
tgacactcca ttggcatcga cggacaccag gcgccg                            36

<210> SEQ ID NO 19
<211> LENGTH: 37
<212> TYPE: DNA
<213> ORGANISM: feline herpesvirus

<400> SEQUENCE: 19
gcgccccaga cgtcgatgaa acaaacctag ccataga                           37

<210> SEQ ID NO 20
<211> LENGTH: 43
<212> TYPE: DNA
<213> ORGANISM: feline herpesvirus

<400> SEQUENCE: 20
tccgtactat ctattgtcga aattcgagct cgcccgggga tcc                    43

<210> SEQ ID NO 21
<211> LENGTH: 31
<212> TYPE: DNA
<213> ORGANISM: Artificial Sequence
<220> FEATURE:
<221> NAME/KEY: misc_feature
<222> LOCATION: ()..()
<223> OTHER INFORMATION: PCR and synthetic primer

<400> SEQUENCE: 21
gcaactgcag caacaatgaa ttcggatccc g                                 31

<210> SEQ ID NO 22
<211> LENGTH: 33
<212> TYPE: DNA
<213> ORGANISM: Artificial Sequence
<220> FEATURE:
<221> NAME/KEY: misc_feature
<222> LOCATION: ()..()
<223> OTHER INFORMATION: PCR and synthetic primer

<400> SEQUENCE: 22
```

-continued

```
cgttctgcag cctctagctt attctagatc ttt                                         33

<210> SEQ ID NO 23
<211> LENGTH: 74
<212> TYPE: DNA
<213> ORGANISM: feline herpesvirus

<400> SEQUENCE: 23
gttcacagta tctactgtgc acctaccccg gggatcctct agagtcgact gcagcaacaa           60
tcaattcgga tccc                                                             74
```

RECOMBINANT FELINE HERPESVIRUS COMPRISING A FOREIGN DNA INSERTED INTO A REGION CORRESPONDING TO A 3.0 KB ECORI-SALI FRAGMENT OF A FELINE HERPESVIRUS GENOME

Throughout this application various publications are referenced by Arabic numerals in brackets. Full citations for these publications may be found at the end of the specification immediately preceding the claims. The disclosures of these publications are in their entirety hereby incorporated by reference into this application to more fully describe the state of the art to which this invention pertains.

BACKGROUND OF THE INVENTION

Herpesviruses contain 100,000 to 200,000 base pairs of DNA as their genetic material having a long unique segment and a short unique segment, the short unique segment bounded by an internal repeat sequence and a terminal repeat sequence. Within a given genome, several regions have been identified that are not essential for the replication of virus in cell culture. Modifications of some of these regions of the DNA have been known to lower the pathogenicity of the virus, i.e., to attenuate the virus when it infects an animal species. For example, inactivation of the thymidine kinase gene of either human herpes simplex virus [1] or pseudorabies virus of swine [2] renders the human herpesvirus less pathogenic in mice and the pseudorabies virus less pathogenic in swine.

Removal of specific regions of the repeat region of a human herpes simplex virus has been shown to render the virus less pathogenic [1, 3]. Furthermore, a repeat region has been identified in Marek's disease virus that is associated with viral oncogenicity [4]. A region in herpesvirus saimiri has similarly been correlated with oncogenicity [5]. Removal of a specific region of the repeat region renders pseudorabies virus less pathogenic (U.S. Pat. No. 4,877, 737). A region in pseudorabies virus has been shown to be deleted in naturally-occurring vaccine strains [6]. These deletions are at least in part responsible for the lack of pathogenicity of these strains. Specific combinations of glycoproteins gene deletions in herpes simplex virus render the herpes simplex virus less pathogenic in mice [see 37 for review]. While, combinations of glycoprotein gene deletions in pseudorabies virus render the pseudorabies virus less pathogenic in swine [see 38 for review].

Herpesviruses contain non-essential regions of DNA in various parts of the genome, and that modification of these regions can attenuate the virus, leading to a non-pathogenic strain from which a vaccine may be derived. The degree of attenuation of the virus is important to the utility of the virus as a vaccine. Deletions which cause too much attenuation of the virus will result in a vaccine that fails to elicit an adequate immune response. Although several examples of attenuating deletions are known, the appropriate combination of deletions for any herpesvirus is not readily apparent.

Feline herpesvirus 1 (FHV) is the causative agent of feline viral rhinotracheitis, an acute upper respiratory disease in cats [7, 8]. Serological studies indicate that 50 to 70% of adult cats have detectable antibodies to the virus [9, 10]. Currently available inactivated and attenuated live virus vaccines reduce disease but do not prevent infection by FHV [11].

The feline herpesvirus is a member of the family herpesviridae, which are commonly known as the herpesviruses and a member of the subfamily alphaherpesvirus with a group D genome [12]. The FHV genome is comprised of approximately 134 kilobase (kb) pairs that is subdivided into a long unique segment of approximately 104 kb and a short unique segment of approximately 8 kb [13]. The unique short region is bounded by inverted repeat sequences which are approximately 11 kb. Physical maps of restriction endonuclease sites of the FHV genome have been published [12, 13]. The thymidine kinase gene of FHV has been sequenced and an FHV virus containing a deletion of the TK gene was isolated using a drug selection technique [14]. A feline herpesvirus having a deletion of the TK gene and an insertion of the feline leukemia virus (FeLV) envelope (env) and gag genes at the TK deletion site has been constructed [36]. Feline herpesviruses containing an insertion in the ORF1 and ORF2 region within the unique short [43], or a deletion in the gI and gE region of the unique short [44] have been described. A feline herpesvirus containing an insertion in a region of the unique long downstream of the FHV gC gene has been constructed [40,45].

The feline herpesviruses in this invention are useful as vectors for the delivery of vaccine antigens from microorganisms causing diseases in animals other than cats or dogs and for the delivery of therapeutic agents. The therapeutic agent that is delivered by a viral vector of the present invention must be a biological molecule that is a by-product of feline herpesvirus replication. This limits the therapeutic agent in the first analysis to either DNA, RNA or protein. There are examples of therapeutic agents from each of these classes of compounds in the form of antisense DNA, antisense RNA [18], ribozymes [19], suppressor tRNAs [20], interferon-inducing double stranded RNA and numerous examples of protein therapeutics, from hormones, e.g., insulin, to lymphokines, e.g., interferons and interleukins, to natural opiates. The discovery of these therapeutic agents and the elucidation of their structure and function does not necessarily allow one to use them in a viral vector delivery system

SUMMARY OF THE INVENTION

This invention provides a recombinant feline herpesvirus comprising a foreign DNA inserted into a feline herpesvirus genome, wherein the foreign DNA is inserted into a region of the genome which corresponds to a 3.0 kb EcoRI-SalI fragment within a SalI A fragment of the feline herpesvirus genome and is capable of being expressed in a host cell into which the virus is introduced.

Further this invention provides a recombinant feline herpesvirus comprising a feline herpesvirus genome, wherein the feline herpesvirus genome contains a deletion in a 3.0 kb EcoRI-SalI fragment of the SalI A fragment of the feline herpesvirus genome.

Lastly, this invention provides vaccines and methods of immunization of animals infected with feline herpesvirus.

BRIEF DESCRIPTION OF THE FIGURES

FIG. 1: Restriction endonuclease map of the feline herpesvirus genome.

FIG. 2: Restriction endonuclease map of the feline herpesvirus 3.0 kb EcoRI to SalI fragment within the SalI A genomic fragment. Three open reading frames have been identified in the 2968 base pair region (SEQ ID NO. 3),: UL 24 (SEQ ID NO. 4), UL 25 (SEQ ID NO. 5), UL 26 (SEQ ID NO. 6).

FIGS. 3A–B: DNA insertion in Homology Vectors 855-30.A4. The diagram shows the orientation of DNA fragments assembled in plasmid 855-30.A4. The source of each fragment is described in the Materials and Methods section. The origin of FHV DNA sequences is from SEQ ID NO: 3. The sequences located at the junctions between fragments are shown (SEQ ID NOS: 13–16 respectively), including junction B (SEQ ID NO: 14), junction E (SEQ ID NO: 15). The restriction endonuclease sites used to generate each fragment as well as the synthetic DNA sequences that were used to join the fragments are described for each junction. The synthetic DNA sequences are underlined by a solid bar. The following convention is used: restriction endonuclease sites in brackets [] indicate the remnants of sites that were destroyed during construction. The DNA insertion of the gX promoter-LacZ PRV gX poly A cassette (Fragments 2, 3, and 4) is described in PCT International Publication WO 96/13575 and is incorporated herein by reference. The following abbreviations are used, feline herpesvirus (FHV), pseudorabies virus (PRV), glycoprotein X (gX), polyadenylation site (poly A), base pairs (BP), E. Coli lacz-beta-galactosidase (lacZ).

Figure 4A:

FIGS. 4A–B: DNA insertion in Homology Vectors 855-30.F9. The diagram shows the orientation of DNA fragments assembled in plasmid 855-30.A4. The source of each The source of each fragment is described in the Materials and Methods section. The origin of FHV DNA sequences is from SEQ ID NO: 3. The sequences located at the junctions between fragments are shown (SEQ ID NOS: 17–20 respectively), including junction B (SEQ ID NO: 18), junction E (SEQ ID NO: 19). The restriction endonuclease sites used to generate each fragment as well as the synthetic DNA sequences that were used to join the fragments are described for each junction. The synthetic DNA sequences are underlined by a solid bar. The following convention is used: restriction endonuclease sites in brackets [] indicate the remnants of sites that were destroyed during construction. The DNA insertion of the gX promoter-lacZ PRV gX poly A cassette (Fragments 2, 3, and 4) is described in PCT International Publication WO 96/13575 and is incorporated herein by reference. The following abbreviations are used, feline herpesvirus (FHV), pseudorabies virus (PRV), glycoprotein X (gX), polyadenylation site (poly A), base pairs (BP), E. Coli lacZ-beta-galactosidase (lacZ).

Figure 5:
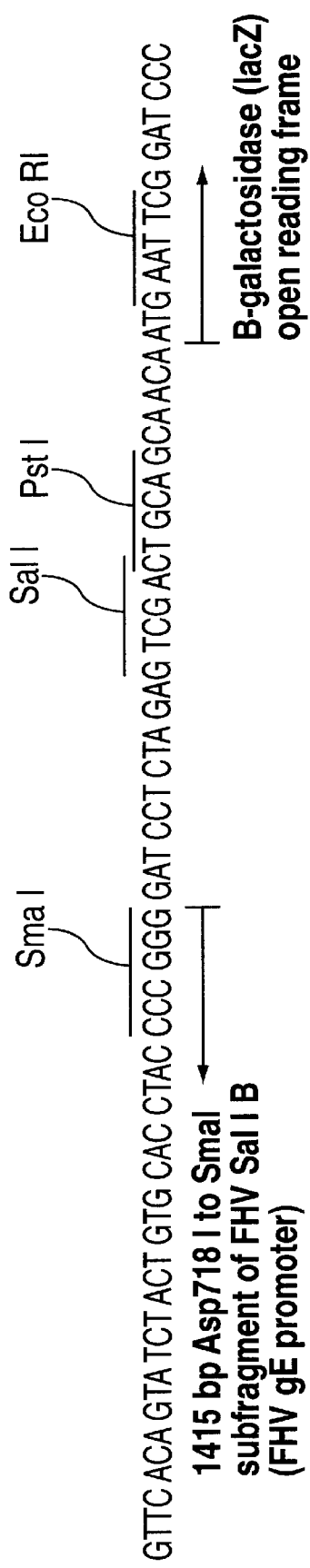

FIG. 5: Junction region between feline herpesvirus glycoprotein E promoter and foreign DNA (lacZ) in homology vector 846-88.B17 and recombinant S-FHV-020 (SEQ ID NO: 23). The FHV gE. promoter is withing an approximately 1415 base pari Asp718 I to SmaI subfragment of the FHV SalI B genomic fragment.

DETAILED DESCRIPTION OF THE INVENTION

The present invention involves a recombinant feline herpesviruse useful in the preparation of vaccines to protect cats from naturally-occuring infectious feline herpesvirus. The present invention is also useful for expression of a foreign DNA or genes from other pathogens for protection against disease. Recombinant feline herpesvirus expressing a foreign DNA from avian or mammalian pathogens are useful as vaccines in avian or mammalian species including but not limited to chickens, turkeys, ducks, feline, canine, bovine, equine, and primate, including human.

This invention provides a recombinant feline herpesvirus comprising a foreign DNA inserted into a feline herpesvirus genome, wherein the foreign DNA is inserted into a region of the genome which corresponds to an approximately 3.0 kb EcoRI-SalI fragment within a SalI A fragment of the feline herpesvirus genome and is capable of being expressed in a host cell into which the virus is introduced.

In one embodiment the foreign DNA is inserted within a UL25 gene within the 3.0 kb EcoRI-SalI fragment. In one embodiment the foreign DNA is inserted within a UL24 gene within the 3.0 kb EcoRI-SalI fragment. In one embodiment the foreign DNA is inserted within a UL26 gene within the 3.0 kb EcoRI-SalI fragment. In one embodiment the foreign DNA is inserted within a intergenic regions within the 3.0 kb EcoRI-SalI fragment. In another embodiment the foreign DNA is inserted within a NdeI site within the approximately 3.0 kb EcoRI-SalI fragment.

The "approximately 3.0 EcoRI-SalI fragment" means a fragment which results from the steps of: a) digesting a feline herpesvirus genome with a SalI restriction endonuclease, b) cloning the resulting fragments in a plasmid, and c) digesting the plasmid containing a SalI A fragment with an EcoRI and SalI restriction endonucleases. In one embodiment the "approximately 3.0 kb EcoRI-SalI fragment" is an EcoRI-SalI fragment from a feline herpesvirus having a 2968 nucleotide acid sequence as set forth in SEQ. ID. NO: 3. It is contemplated by this invention that the "approximately 3.0 EcoRI-SalI fragment" is an EcoRI-SalI fragment which is homologous to the EcoRI-SalI fragment of the 2968 kb EcoRI-SalI fragment from the NVSL strain.

For purposes of this invention, "a recombinant feline herpesvirus" is a live feline herpesvirus which has been generated by the recombinant methods well known to those of skill in the art, e.g., the methods set forth in HOMOLOGOUS RECOMBINATION PROCEDURE FOR GENERATING RECOMBINANT HERPESVIRUS Materials and Methods, and the virus has not had genetic material essential for the replication of the feline herpesvirus deleted.

This invention provides a recombinant feline herpesvirus comprising a foreign DNA inserted within a non-essential region of the feline herpesvirus genome, wherein the foreign DNA is inserted into a region corresponding to a 5.0 kb fragment of the unique long region which is within a SalI H fragment of the feline herpesvirus genome.

This invention provides a recombinant feline herpesvirus comprising a foreign DNA inserted within a non-essential region of the feline herpesvirus genome, wherein the foreign DNA is inserted into a SalI M fragment of the feline herpesvirus genome.

This invention provides a recombinant feline herpesvirus comprising a foreign DNA inserted within a non-essential region of the feline herpesvirus genome, wherein the foreign DNA is inserted into SalI N fragment of the feline herpesvirus genome.

This invention provides a recombinant feline herpesvirus further comprising a second foreign DNA inserted within a non-essential region of the feline herpesvirus genome. The second foreign DNA may be inserted into a unique short region of the feline herpesvirus genome. In one embodiment the the second foreign DNA may be inserted into a glycoprotein E gene. In another embodiment the second foreign DNA may be inserted into a glycoprotein I gene. In another embodiment the second foreign DNA may be inserted into a glycoprotein G gene. The second foreign DNA may be inserted into a unique long region of the feline herpesvirus genome.

This invention provides the insertion of multiple foreign DNAs into non-essential regions of the feline herpesvirus genome. Further, this invention provides multiple foreign DNAs inserted into one site or region of the non-essential region of the feline herpesvirus genome or in different regions of the feline herpesvirus genome.

This invention provides a recombinant feline herpesvirus further comprising a deletion in a non-essential region of the feline herpesvirus genome. In one embodiment the deletion is in the unique short region. In another embodiment the deletion is in the glycoprotein E gene. In another embodiment the deletion is in the glycoprotein I gene. In another embodiment the deletion is in a glycoprotein G gene. In another embodiment the deletion is in the unique long region.

As defined herein, "viral genome" or "genome" means the entire DNA which naturally occurrs in the feline virus. As defined herein, "foreign DNA" or "foreign gene" means any DNA or gene that is exogenous to the genome.

As defined herein "a non-essential site" or "a non-essential region" in the feline herpesvirus genome means a region or site in the viral genome which is not necessary for the viral infection or replication.

In one embodiment the polypeptide is a detectable marker. For purposes of this invention, a "polypeptide which is a detectable marker" includes the diner, trimer and tetramer form of the polypeptide. *E. coli* B-galactosidase is a tetramer composed of four polypeptides or monomer subunits. In one embodiment the polypeptide is *E. coli* beta-galactosidase.

In one embodiment the foreign DNA encodes a polypeptide. In another embodiment the polypeptide is antigenic. In one embodiment foreign DNA encodes Marek's Disease Virus glycoprotein A, Marek's Disease Virus glycoprotein B or Marek's Disease Virus glycoprotein D. In one embodiment foreign DNA encodes Newcastle Disease Virus fusion protein or Newcastle Disease Virus hemagglutinin-neuraminidase.

In one embodiment foreign DNA encodes Infectious Laryngotracheitis Virus glycoprotein B, Infectious Laryngotracheitis Virus glycoprotein I or Infectious Laryngotracheitis Virus glycoprotein D. In one embodiment foreign DNA encodes Infectious Bronchitis Virus spike protein or Infectious Bronchitis Virus matrix protein. In one embodiment foreign DNA encodes Infectious Bursal Disease virus VP2, Infectious Bursal Disease virus VP3, or Infectious Bursal Disease virus VP4.

In one embodiment foreign DNA is selected from a group consisting of Feline Leukemia virus envelope gene,Feline Leukemia virus protease (gag) gene, Hepatitis B core antigen gene, Pseudorabies virus glycoprotein C gene, *Dirofilaria immitis* 22 kD, *Dirofilaria immitis* p39 gene, Feline Immunodeficiency virus gag, Feline Immunodeficiency Virus pol gene, and Feline Immunodeficiency Virus env gene.

Such antigenic polypeptide may be derived or derivable from the following: feline pathogen, canine pathogen, equine pathogen, bovine pathogen, avian pathogen, porcine pathogen, or human pathogen.

In another embodiment, the antigenic polypeptide of a human pathogen is derived from human herpesvirus, herpes simplex virus-1, herpes simplex virus-2, human cytomegalovirus, Epstein-Barr virus, Varicell-Zoster virus, human herpesvirus-6, human herpesvirus-7, human influenza, human immunodeficiency virus, rabies virus, measles virus, hepatitis B virus and hepatitis C virus. Furthermore, the antigenic polypeptide of a human pathogen may be associated with malaria or malignant tumor from the group consisting of Plasmodium falciparum, Bordetella pertusis, and malignant tumor.

The antigenic polypeptide of an equine pathogen can derived from equine influenza virus or equine herpesvirus. Examples of such antigenic polypeptide are equine influenza virus type A/Alaska 91 neuraminidase, equine influenza virus type A/Prague 56 neuraminidase, equine influenza virus type A/Miami 63 neuraminidase, equine influenza virus type A/Kentucky 81 neuraminidase, equine herpesvirus type 1 glycoprotein B, and equine herpesvirus type 1 glycoprotein D.

The antigenic polypeptide of derived from bovine respiratory syncytial virus equine pathogen can derived from equine influenza virus is bovine respiratory syncytial virus attachment protein (BRSV G), bovine respiratory syncytial virus fusion protein (BRSV F), bovine respiratory syncytial virus nucleocapsid protein (BRSV N), bovine parainfluenza virus type 3 fusion protein, and the bovine parainfluenza virus type 3 hemagglutinin neuraminidase In one embodiment the polypeptide is derived or derivable from the group consisting of: avian encephalomyelitis virus, avian reovirus, avian paramyxovirus, avian influenza virus, avian adenovirus, fowl pox virus, avian coronavirus, avian rotavirus, chick anemia virus (agent), Salmonella spp. *E. coli*, Pasteurella spp., Bordetella spp., Eimeria spp., Histomonas spp., Trichomonas spp., Poultry nematodes, cestodes, trematodes, poultry mites/lice, poultry protozoa.

In one embodiment foreign DNA encodes a cytokine. In another embodiment the cytokine is chicken myelomonocytic growth factor (cMGF), chicken interferon (cIFN) or quail interferon. For example, the cytokine may be, but is not limited to, interleukin-1–interleukin-15, interferons, quail interferon, chicken intereferon, granulocyte-macrophage colony stimulating factors, granulocyte colony stimulating factors and interleukin receptors, TNF, Interferon, and Stem Cell Factor.

In one embodiment foreign DNA is under control of an endogenous upstream promoter. In another embodiment foreign DNA is under control of a heterologous upstream promoter. In another embodiment the promoter is selected from the group consisting of: Feline Herpesvirus glycoprotein E promoter, Pseudorabies virus glycoprotein X promoter, Herpes Simplex Virus-1 alpha 4 promoter, Human Cytomegalovirus immediate early promoter, Marek's Disease Virus glycoprotein A promoter, Marek's Disease Virus glycoprotein B promoter, Marek's Disease Virus glycoprotein D promoter, Infectious Laryngotracheitis Virus glycoprotein B promoter, Infectious Laryngotracheitis Virus glycoprotein D promoter, and Bovine Herpesvirus-1.1 VP8 promoter and chicken anemia virus promoter.

This invention provides a recombinant feline herpesvirus designated S-FHV-020 (ATCC Accession Number VR 2573). This invention provides a recombinant feline herpesvirus of claim 1 designated S-FHV-025. This invention provides a recombinant feline herpesvirus of claim 1 designated S-FHV-026.

S-FHV-020 was deposited on May 9, 1997 under ATCC Accession No. VR 2573 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A.

This invention provides a recombinant herpesvirus comprising a foreign DNA inserted into a herpesvirus genome, wherein the foreign DNA is inserted into a non-essential region and is under the control of a feline herpesvirus glycoprotein E promoter. In one embodiment the foreign DNA is capable of being expressed in a host cell into which the virus is introduced. In one embodiment the herpesvirus is a feline herpesvirus.

This invention provides a recombinant feline herpesvirus comprising a feline herpesvirus genome, wherein the feline herpesvirus genome contains a deletion in a region corresponding to a 3.0 kb EcoRI-SalI fragment of the SalI A fragment of the feline herpesvirus genome.

In one embodiment the deletion is in a UL25 gene within a 3.0 kb EcoRI-SalI fragment. In another embodiment the deletion is in a region which correspond to a SacII—SacII fragment within the 3.0 kb EcoRI-SalI fragment. This invention provides for three such regions which correspond to a SacII-SacII fragment within the 3.0 kb EcoRI-SalI fragment. For example, a region is between nucleotide sequence 1049–1361 of SEQ.ID. No: 3; a region is between nucleotide sequence 1361–1928 of SEQ.ID. No: 3; and a region is between nucleotide sequence 1049–1928 of SEQ.ID. No: 3.

This invention provides a recombinant feline herpesvirus further comprising an insertion of a foreign DNA into a non-essential region of the feline herpesvirus genome. In another embodiment this invention provides a recombinant feline herpesvirus wherein the foreign DNA is a fusion protein of two or more foreign DNAs.

The present invention provides a recombinant feline herpesvirus comprising a feline herpesvirus genome which contains a deletion in the unique short region of the viral genome, wherein the deletion is in the glycoprotein E gene. Said recombinant feline herpesvirus contains a deletion which attenuates the virus, rendering it suitable for use as a vaccine against feline herpesvirus.

In one embodiment the feline herpesvirus contains a foreign DNA inserted into a non-essential region of the feline herpesvirus genome. In another embodiment the foreign DNA is inserted into a unique short region of the feline herpesvirus. In another embodiment the foreign DNA sequence is inserted in the deleted gE gene.

The present invention further provides a recombinant feline herpesvirus comprising the feline herpesvirus viral genome which contains a deletion or other alteration in the unique short region of the viral genome, wherein the deletion or alteration is in the glycoprotein gE gene, so that upon replication, the recombinant virus produces no glycoprotein gE.

The present invention further provides a recombinant feline herpesvirus comprising the feline herpesvirus viral genome which contains a deletion or other alteration in the unique short region of the viral genome, wherein the deletion or alteration is in the glycoprotein gI gene, so that upon replication, the recombinant virus produces no glycoprotein gI.

The present invention further provides a recombinant feline herpesvirus comprising the feline herpesvirus viral genome which contains a deletion or other alteration in the unique short region of the viral genome, wherein the deletion or alteration is in the glycoprotein gG gene and in the glycoprotein gI gene, so that upon replication, the recombinant virus produces no glycoprotein gG and no glycoprotein gI.

It is contemplated that a deletion in any one the above genes will attenuate the virus, rendering it suitable to be used as a vaccine against feline herpesvirus. A foreign DNA sequence may be inserted within any one of these sites in such a way that it may be expressed in a host cell which is infected which the recombinant feline herpesvirus of the present invention.

The present invention further provides a homology vector for producing a recombinant feline herpesvirus by inserting a foreign DNA into the feline herpesvirus genome which comprises a double-stranded DNA molecule consisting of: a) double-stranded foreign DNA sequence encoding an antigenic polypeptide derived from a feline pathogen; b) at one end of the foreign DNA, double-stranded feline virus genome homologous to the genome located at one side of a non-essential site of the feline herpes viral genome; c) at the other end of the foreign DNA sequence, double stranded feline herpesvirus genome homologous to the genome located at the other side of the same site.

For purposes of this invention, a "homology vector" is a plasmid constructed to insert foreign DNA in a specific site on the genome of a feline herpesvirus.

It is contemplated by this invention that the homology vector include the foreign DNA and antigenic polypeptides which are listed hereinabove.

For example, the double stranded foreign DNA of the homology vector encodes an antigenic polypeptide derived from bovine respiratory syncytial virus or bovine parainfluenza virus. The antigenic polypeptide of derived from bovine respiratory syncytial virus equine pathogen can derived from equine influenza virus is bovine respiratory syncytial virus attachment protein (BRSV G), bovine respiratory syncytial virus fusion protein (BRSV F), bovine respiratory syncytial virus nucleocapsid protein (BRSV N), bovine parainfluenza virus type 3 fusion protein, and the bovine parainfluenza virus type 3 hemagglutinin neuraminidase.

In another embodiment the double stranded foreign DNA in the homology vector encodes a cytokine capable of stimulating human immune response. For example, the cytokine may be, but is not limited to, interleukin-2, interleukin-6, interleukin-12, interferons, granulocyte-macrophage colony stimulating factors, and interleukin receptors.

The present invention further provides a homology vector for producing a recombinant feline herpesvirus by inserting a foreign DNA into the feline herpesvirus genome which comprises a double-stranded DNA molecule consisting of: a) double-stranded foreign DNA encoding an antigenic polypeptide derived from a cytokine capable of stimulating an immune response; b) at one end of the foreign DNA, double-stranded feline herpesvirus genome homologous to the genome located at one side of a non-essential site of the feline herpesvirus genome; c) at the other end of the foreign DNA, double stranded feline virus genome homologous to the genome located at the other side of the same site.

The present invention further provides a host cell infected with the recombinant feline herpesvirus. In one embodiment the host cell is a mammalian cell. Other host cells are known to those skilled in the art.

The present invention further provides a vaccine for feline herpesvirus which comprises an effective immunizing amount of the recombinant feline herpesvirus and a suitable carrier. In one embodiment the vaccine against an feline pathogen comprises an effective immunizing amount of the recombinant feline herpesvirus and a suitable carrier. This vaccine may contain either inactivated or live recombinant virus.

Suitable carriers for the recombinant virus are well known to those skilled in the art and include but are not limited to proteins, sugars, etc. One example of such a suitable carrier is a physiologically balanced culture medium containing one or more stabilizing agents such as hydrolyzed proteins, lactose, etc. Preferably, the live vaccine is created by taking tissue culture fluids and adding stabilizing agents such as stabilizing, hydrolyzed proteins. Preferably, the inactivated vaccine uses tissue culture fluids directly after inactivation of the virus.

The present invention further provides a method of immunizing an animal against a human pathogen which comprises administering to the animal an effective immunizing dose of the feline herpes vaccine. In one embodiment the method of immunizing an animal against an feline pathogen comprises administering to the animal an effective immunizing dose of the feline herpes vaccine.

This invention provides a vaccine which comprises an effective immunizing amount of the recombinant feline herpesvirus and a suitable carrier. In one embodiment the carrier is a physiologically balanced culture medium containing stabilizing agents.

The present invention further provides a multivalent vaccine for feline herpesvirus and for one or more of other feline diseases which comprises an effective immunizing amount of a recombinant virus comprising the feline herpesvirus viral genome which contains a deletion in the unique short region, wherein the deletion is in the glycoprotein E gene, and an insertion of a foreign gene into a non-essential site of the viral genome.

The present invention further provides a vaccine which comprises a suitable carrier and an effective immunizing amount of a recombinant feline herpesvirus comprising the feline herpesvirus viral genome which contains a deletion or other alteration in the unique short region of the viral genome, wherein the deletion or alteration is in the glycoprotein E gene so that upon replication, the recombinant virus produces no glycoprotein E.

For purposes of this invention, an "effective immunizing amount" of the recombinant feline herpesvirus of the present invention is within the range of $10^3$ to $10^9$ PFU/dose. In another embodiment the immunizing amount is $10^5$ to $10^7$ PFU/dose. In a preffered embodiment the immunizing amount is $10^6$ PFU/dose.

The method comprises administering to the animal an effective immunizing dose of the vaccine of the present invention. The vaccine may be administered by any of the methods well known to those skilled in the art, for example, by intramuscular, subcutaneous, intraperitoneal or intravenous injection. Alternatively, the vaccine may be administered intranasally or orally, intradermal, inovo, or ocularly.

This invention provides a method of immunizing an animal against an animal pathogen which comprises administering to the animal an effective immunizing dose of the vaccine. This invention provides a multivalent vaccine which comprises an effective immunizing amount of the recombinant feline herpesvirus.

The present invention also provides a method of immunizing an animal, wherein the animal is a feline, canine, ovine, bovine, caprine, swine or human. For purposes of this invention, this includes immunizing the animal against the virus or viruses which cause the disease or diseases feline herpesvirus.

The present invention further provides a method of distinguishing an animal vaccinated with a feline herpesvirus from an animal infected with a naturally-occuring feline herpesvirus which comprises analysing a sample of a body fluid from the animal for the presence of feline herpesvirus gE and at least one other antigen normally expressed in an animal infected by a naturally-occuring feline herpesvirus, determining whether the antigen and gE are present in the body fluid, the presence of the antigen and the absence of gE indicative of an animal vaccinated with the vaccine and not infected with a naturally-occuring feline herpesvirus.

In one embodiment the presence of the antigen and of gE in the body fluid is determined by detecting in the body fluid antibodies specific for the antigen and for gE.

The present invention provides a method for testing a feline to determine whether the feline has been vaccinated with the vaccine of the present invention, particularly the embodiment which contains the recombinant feline herpesvirus S-FHV-020 or S-FHV-025.

This invention is further illustrated in the Experimental Details section which follows. This section is set forth to aid in an understanding of the invention but is not intended to, and should not be construed to, limit in any way the invention as set forth in the claims which follow thereafter.

EXPERIMENTAL DETAILS:

Materials and Methods

PREPARATION OF FHV VIRUS STOCK SAMPLES:S-FHV-000 was obtained from the ATCC (ATCC No. 636) and S-FHV-001 was obtained from the NVSL (NVSL Challange Virus Strain SGE, Lot KS). FHV virus stock samples were prepared by infecting Crandell Feline Kidney (CRFK) cells at a multiplicity of infection of 1.0 PFU/cell in Dulbecco's Modified Eagle Medium (DMEM) containing 2 mM glutamine, 100 units/ml penicillin, 100 units/ml streptomycin (these components were obtained from Irvine Scientific or equivalent supplier, and hereafter are referred to as complete DME medium) plus 5% fetal bovine serum. After cytopathic effect was complete, the medium and cells were harvested, aliquoted and frozen at −70° C. The titers were approximately $1 \times 10^7$ to $1 \times 10^8$ PFU/ml.

PREPARATION OF HERPESVIRUS DNA:A confluent monolayer of CRFK cells in a 25 cm² flask or 60 mm petri dish was infected with 100 ml of virus sample. After overnight incubation, or when the cells were showing 100% cytopathic effect, the cells were scraped into the medium. The cells and medium were centrifuged at 3000 rpm for 5 minutes in a clinical centrifuge. The medium was decanted, and the cell pellet was gently resuspended in 0.5 ml solution containing 0.5% NONIDET P-40® (octyl phenol ethylene oxide condensate containing an average of 9 moles of ethylene oxide per molecule) (NP-40®, purchased from Sigma Chemical Co., St. Louis, Mo.). The sample was incubated at room temperature for 10 minutes. Ten ml of a stock solution of RNase A (Sigma Chemical Co., St. Louis, Mo.) were added (stock was 10 mg/ml, boiled for 10 minutes to inactivate DNAse). The sample was centrifuged to pellet nuclei. The DNA pellet was removed with a pasteur pipette or wooden stick and discarded. The supernatant fluid was decanted into a 1.5 ml Eppendorf tube containing 25 ml of 20% sodium dodecyl sulfate (Sigma) and 25 ml proteinase-K (10 mg/ml; Boehringer Mannheim Biochemicals, Indianapolis, Ind.). The sample was mixed and incubated at 37° C. for 30–60 minutes. An equal volume of water-saturated phenol was added and the sample was mixed briefly. The sample was centrifuged in an Eppendorf minifuge for 5 minutes at full speed. The upper aqueous phase was removed to a new Eppendorf tube, and two volumes of absolute ethanol were added and the tube put at −20° C. for 30 minutes to precipitate nucleic acid. The sample was centrifuged in an Eppendorf minifuge for 5 minutes. The supernatant was decanted, and the pellet was air dried and rehydrated in ~16 ml H₂O. For the preparation of larger amounts of DNA, the procedure was scaled up to start with roller bottles or 175 cm² flasks of CRFK cells. The DNA was stored in 0.01 M tris pH 7.5, 1 mM EDTA at 4° C.

MOLECULAR BIOLOGICAL TECHNIQUES:Techniques for the manipulation of bacteria and DNA, including such procedures as digestion with restriction endonucleases, gel electrophoresis, extraction of DNA from gels, ligation, phosphorylation with kinase, treatment with phosphatase, growth of bacterial cultures, transformation of bacteria with DNA, and other molecular biological methods are described in [22 and 23]. The polymerase chain reaction (PCR) was used to introduce restriction endonuclease sites convenient for the manipulation of various DNAs [24]. In general, amplified fragments were less than 500 base pairs in size and critical regions of amplified fragments were confirmed by DNA sequencing. Except as noted, these techniques were used with minor variations.

LIGATION:DNA was joined together by the action of the enzyme T4 DNA ligase (BRL). Ligation reactions contained various amounts of DNA (from 0.2 to 20 mg), 20 mM Tris pH 7.5, 10 mM $MgCl_2$, 10 mM dithiothreitol (DTT), 200 mM ATP and 20 units T4 DNA ligase in 10–20 ml final reaction volume. The ligation proceeded for 3–16 hours at 15° C.

DNA SEQUENCING:Sequencing was performed using the USB Sequenase Kit and $^{35}$S-dATP (NEN). Reactions using both the dGTP mixes and the dITP mixes were performed to clarify areas of compression. Alternatively, compressed areas were resolved on formamide gels. Templates were double-stranded plasmid subclones or single stranded M13 subclones, and primers were either made to the vector just outside the insert to be sequenced, or to previously obtained sequence. Alternatively, DNA sequencing was performed on the Applied Biosystems Automated Sequencer Model 388A per instructions of the manufacturer using Taq DNA polymerase and fluorescently-labelled dideoxynucleotides. The sequence obtained was assembled and compared using DNAStar software. Subsequent manipulation and comparison of sequences obtained was performed with Superclone and Supersee programs from Coral Software and DNAStar.

SOUTHERN BLOTTING OF DNA:The general procedure for Southern blotting was performed as in Maniatis et al. and Sambrook et al. [22, 23]. DNA was blotted to nitrocellulose filters and hybridized to appropriately labeled DNA probes. Probes for Southern blots were prepared using either the Nonradioactive DNA Labeling and Detection Kit of Boehringer Mannheim or the nick translation kit of Bethesda Research Laboratories (BRL). In both cases the manufacturer's recommended procedures were followed.

DNA TRANSFECTION FOR GENERATING RECOMBINANT VIRUS:The method is based upon the calcium phosphate procedure of Graham and Van der eb [25] with the following modifications. Virus and/or Plasmid DNA were diluted to 298 ml in 0.01 M Tris pH 7.5, 1 mM EDTA. Forty ml 2M $CaCl_2$ was added followed by an equal volume of 2× HEPES buffered saline (10 g N-2-hydroxyethyl piperazine N'-2-ethanesulfonic acid (HEPES), 16 g NaCl, 0.74 g KCl, 0.25 g $Na_2HPO_4$—$2H_2O$, 2 g dextrose per liter $H_2O$ and buffered with NaOH to pH 7.4). The mixture was then incubated on ice for 10 minutes, and then added dropwise to an 80% confluent monolayer of CRFK cells growing in a 60 mm petri dish under 5 ml of medium (DME plus 5% fetal bovine serum). The cells were incubated 4 hours at 37° C. in a humidified incubator containing 5% $CO_2$. Media on the plates were aspirated, and cells were treated with 20% glycerol in 1×XPBS (1.15 g $Na_2HPO_4$, 0.2 g $KH_2PO_4$, 0.8 g NaCl, 0.2 g KCl per liter $H_2O$) for one minute. The cells were washed three times with 5 ml of 1×PBS and then fed with 5 ml of medium (DME plus 5% fetal bovine serum). The cells were incubated at 37° C. as above for 3–7 days until cytopathic effect from the virus was 50–100%. Virus was harvested as described above for the preparation of virus stocks. This stock was referred to as a transfection stock and was subsequently screened for recombinant virus by the SCREEN FOR RECOMBINANT HERPESVIRUS EXPRESSING ENZYMATIC MARKER GENES.

HOMOLOGOUS RECOMBINATION PROCEDURE FOR GENERATING RECOMBINANT HERPESVIRUS:This method relies upon the homologous recombination between herpesvirus DNA and plasmid homology vector DNA which occurs in tissue culture cells co-transfected with these elements. From 0.1–1.0 mg of plasmid DNA containing foreign DNA flanked by appropriate herpesvirus cloned sequences (the homology vector) were mixed with approximately 0.3 mg of intact herpesvirus DNA. The DNAs were diluted to 298 ml in 0.01 M Tris pH 7.5, 1 mM EDTA and transfected into CRFK cells according to the DNA TRANSFECTION FOR GENERATING RECOMBINANT VIRUS (see above).

DIRECT LIGATION PROCEDURE FOR GENERATING RECOMBINANT HERPESVIRUS:Rather than using homology vectors and relying upon homologous recombination to generate recombinant virus, we have also developed the technique of direct ligation to engineer herpesviruses. In this instance, a cloned foreign gene did not require flanking herpesvirus DNA sequences but only required that it have restriction endonuclease sites available to cut out the foreign gene fragment from the plasmid vector. A compatible restriction enzyme was used to cut herpesvirus DNA. A requirement of the technique is that the restriction enzyme used to cut the herpesvirus DNA must cut at a limited number of sites. For FHV the restriction enzymes SfiI in S-FHV-010 is appropriate. Restriction endonuclease sites previously introduced into herpesviruses by other methods may also be used. The herpesvirus DNA is mixed with a 30-fold molar excess of plasmid DNA (typically 5 mg of virus DNA to 10 mg of plasmid DNA), and the mixture is cut with the appropriate restriction enzyme. The DNA mixture is phenol extracted and ethanol precipitated to remove restriction endonucleases, and ligated together according to the ligation procedure detailed above. The ligated DNA mixture is then resuspended in 298 ml 0.01 M Tris pH 7.5, 1 mM EDTA and transfected into CRFK cells according to the DNA TRANSFECTION FOR GENERATING RECOMBINANT VIRUS (see above). PROCEDURE FOR GENERATING RECOMBINANT HERPESVIRUS FROM SUBGENOMIC DNA FRAGMENTS:The ability to generate herpesviruses by cotransfection of cloned overlapping subgenomic fragments is known to those skilled in the art [26, 27]. If deletions and/or insertions are engineered directly into the subgenomic fragments prior to the cotransfection, this procedure results in a high frequency of viruses containing the genomic alteration, greatly reducing the amount of screening required to purify the recombinant virus. In the first step of this procedure deletions are introduced into separate viruses via homologous recombination with enzymatic marker genes as described below. The homology vector used in this step is constructed such that the enzymatic marker gene is flanked by a restriction endonuclease site that does not cut FHV in the region of the DNA to be deleted. In the second step a library of overlapping subgenomic fragments, capable of regenerating wild-type virus, is constructed from randomly sheared S-FHV-001 DNA. In the third step subgenomic fragments are cloned from each of the individual recombinant viruses containing attenuating deletion/marker gene insertions, which were generated in the first step. In each case the subcloned fragment corresponds in size and location to one of the wildtype subgenomic fragments constructed in the second step. This is accomplished by screening a library of randomly sheared recombinant virus DNA subclones with probes generated from the ends of the appropriate wildtype subgenomic fragment. The restriction endonuclease sites which had been engineered to flank the marker genes in the first step are now utilized to replace the marker genes in each subgenomic fragment with various foreign genes (such as FeLV env, FIV env, FIV gag, *D. immitis* DiPLA2). In the fourth step cotransfection of the appropriate overlapping wild type and deletion/insertion derived subgenomic fragments permits the generation of recombinant FHV viruses incorporating any desired combination of deletions and/or insertions.

SCREEN FOR RECOMBINANT HERPESVIRUS EXPRESSING AN ENZYMATIC MARKER GENE:When the *E.coli* β-galactosidase (lacZ) marker gene was incorporated into a recombinant virus the plaques containing recombinants were visualized by a simple assay. The enzymatic substrate was incorporated (300 mg/ml) into the agarose overlay during the plaque assay. For the lacZ marker gene the substrate BLUOGAL™ (halogenated indolyl-β-D-galactoside, Life Technologies, Inc., Bethesda, Md.) was used. Virus that expressed active marker enzyme turned blue. The blue plaques were then picked onto fresh CRFK cells, and the recombinant virus was purified by further blue plaque isolation. For recombinant virus construction in which the strategy requires that the enzymatic marker gene be removed, a subsequent assay involved plaque purifying white plaques from a background of parental blue plaques. In both cases viruses were typically purified with three to five sequential rounds of plaque purification.

CONSTRUCTION OF DELETION VIRUSES:The strategy used to construct viruses containing genomic deletions involved the use of either homologous recombination and/or direct ligation techniques. Initially a virus was constructed via homologous recombination, in which the DNA to be deleted was replaced with a marker gene such as *E.coli* β-galactosidase (lacZ). A second virus was then constructed in which the marker gene was subsequently deleted either by homologous recombination or via direct ligation. The advantage of this strategy is that both viruses may be purified by the SCREEN FOR RECOMBINANT HERPESVIRUS EXPRESSING ENZYMATIC MARKER GENES. The first virus is purified by picking blue plaques from a white plaque background, the second virus is purified by picking white plaques from a blue plaque background.

SCREEN FOR FOREIGN GENE EXPRESSION IN RECOMBINANT FHV USING BLACK PLAQUE ASSAYS: To analyze expression of foreign antigens expressed by recombinant FHV, monolayers of CRFK cells are infected with recombinant FHV, overlaid with nutrient agarose media and incubated for 1–2 days at 37° C. Once plaques have developed, the agarose overlay was removed from the dish, the monolayer rinsed once with PBS, fixed with 100% methanol for 10 minutes at room temperature and the cells air dried. After re-hydrating the plate with PBS, the primary antibody was diluted to the appropriate dilution with PBS plus Blotto and incubated with the cell monolayer for 2 hours to overnight at room temperature. Unbound antibody was removed from the cells by washing four times with PBS at room temperature. The appropriate secondary antibody conjugate was diluted 1:500 with PBS and incubated with the cells for 2 hours at room temperature. Unbound secondary antibody was removed by washing the cells three times with PBS at room temperature. The monolayer was rinsed in color development buffer (100 mM Tris pH 9.5/100 mM NaCl/5 mM MgCl2), and incubated 10 minutes to overnight at room temperature with freshly prepared substrate solution (0.3 mg/ml Nitro Blue tetrazolium+0.15 mg/ml 5-Bromo-4-Chloro-3-Indolyl Phosphatase in color development buffer). the reaction was stopped by replacing the substrate solution with TE (10 mM Tris, pH7.5/1 mM EDTA). Plaques expressing the correct antigen stain black.

WESTERN BLOTTING PROCEDURE: Samples of lysates and protein standards were run on a polyacrylamide gel according to the procedure of Laemnli [39]. After gel electrophoresis the proteins were transferred and processed according to Sambrook et al. [23]. The primary antibody was diluted 1:100 with 5% non-fat dry milk in Tris-sodium chloride, and Sodium Azide (TSA: 6.61 g Tris-HCl, 0.97 g Tris-base, 9.0 g NaCl and 2.0 g Sodium Azide per liter $H_2O$). The secondary antibody was a alkaline phosphatase conjugate diluted 1:1000 with TSA.

ELISA ASSAY: Indirect Elisa assay was performed using standard techniques as described [35].

SERUM-VIRUS NEUTRALIZATION ASSAY: Sera were tested for FHV- and FeLV-specific antibodies by a microtiter technique. Test serum was inactivated for 30 minutes at 56° C. Duplicate 2-fold dilutions of test sera were made in 96-well microtitration plates with a 25 ml pipettor. Equal volumes of virus suspension containing approximately 300 PFU were added to individual wells and the serum/virus mixtures were incubated at 37° C. for 1 hour. 0.05 ml of a CRFK cell suspension containing approximately $4\times10^5$ cells/ml was added to each well. The presence of antibody was indicated by the formation of a complete monolayer in 48 hours.

HOMOLOGY VECTOR HOMOLOGY VECTOR 885-30.A4:The homology vector 885-30.A4 was constructed for the purpose of inserting a foreign DNA into an approximately 2968 base pair EcoRI to SalI region of the SalI A genomic fragment of the feline herpesvirus (FHV) genome the feline herpesvirus (SEQ ID NO. 3). It incorporates an *E. Coli* β-galactosidase gene flanked by FHV DNA. The foreign genes were inserted into an approximately 878 base pair deletion (Sac II to Sac II; Nucl. 1049 t 1928, SEQ ID NO. 3) within the approximately 2968 base pair EcoRI to SalI fragment. A detailed description of the plasmid is given in FIG. 4. Homology vector 885-30.A4 was constructed from the indicated DNA sources utilizing standard recombinant DNA techniques [22,23]. The plasmid vector is derived from an approximately 2996 base pair EcoRI to SalI restriction endonuclease fragment of a pSP65. Fragment 1 is an approximately 1031 base pair EcoRI to SacI subfragment of the FHV SalI A fragment. Fragment 2 is an approximately 423 base pair Sall to BanHI subfragment of PRV BamHI to PvuII subfragment of pJF751 [28]. Fragment 4 is an approximately 751 base pair SacII to Sall subfragment of PRV BamHI #7[29]. Fragment 5 is an approximately 1039 base pair NdeI to SalI subfragment of the FHV SalI A fragment.

HOMOLOGY VECTOR 885-30.F9:The homology vector 885-30.F9 was constructed for the purpose of inserting a foreign DNA into a 2968 base pair EcoRI to SalI fragment of the SalI. A genomic fragment of the FHV genome the feline herpesvirus (SEQ ID NO. 3). It incorporates an *E. Coli* β-galactosidase gene flanked by FHV DNA. The foreign genes were inserted into a unique NdeI site (Nucl. 1305; SEQ ID NO. 3) within the 2968 base pair EcoRI to SalI fragment. A detailed description of the plasmid is given in FIG. 5. Homology vector 885-30. F9 was constructed from the indicated DNA sources utilizing standard recombinant DNA techniques [22,23]. The plasmid vector is derived from an approximately 2966 base pair EcoRI to SalI restriction endonuclease fragment of a pSP65. Fragment 1 is an approximately 1342 base pair EcoRI to NdeI subfragment of the FHV SalI A fragment. Fragment 2 is an approximately 751 base pair NdeI to SalI subfragment of PRV BamHI #7[29]. Fragment 3 is an approximately 3006 base pair BamHI to PvuII subfragment of pJF751[28]. Fragment 4 is an approximately 423 base pair SalI to BamHI subfragment of PRV BamHI #10[29]. Fragment 5 is an approximately 1659 base pair NdeI to SalI subfragment of the FHV SalI A fragment.

Figure 1:
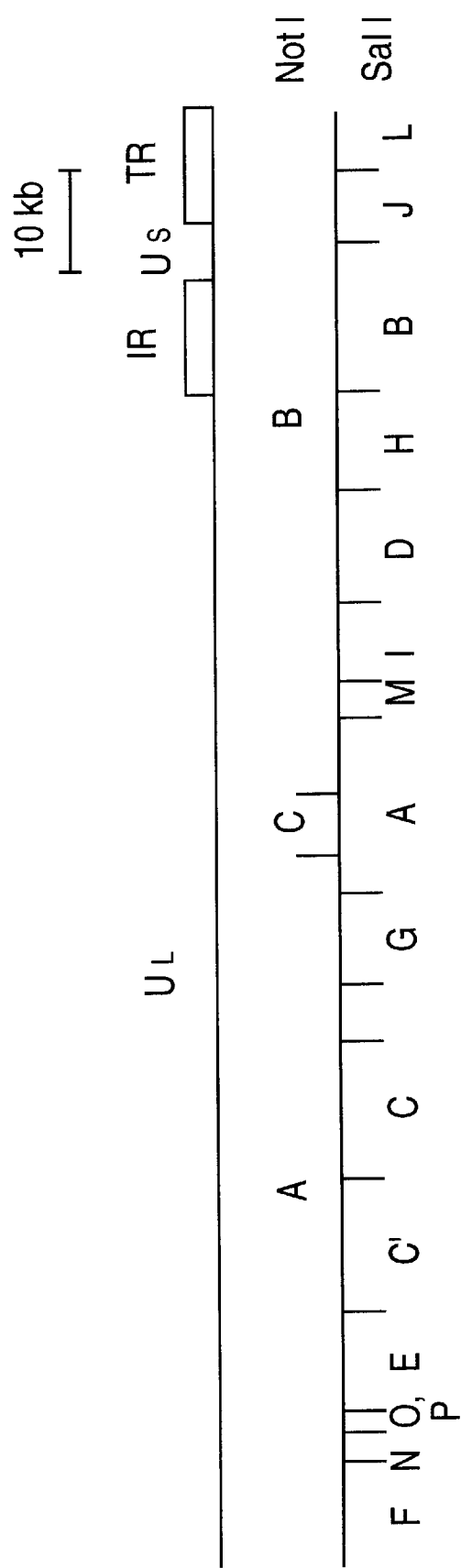
Figure 2:
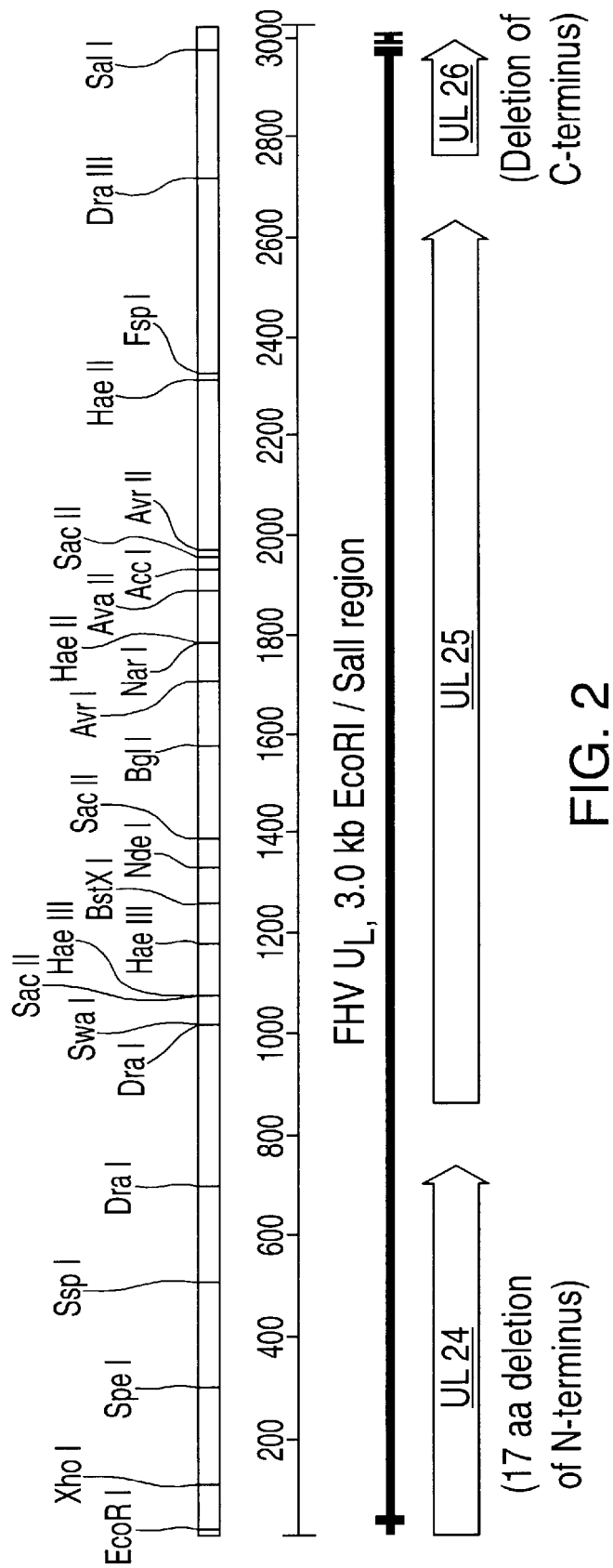
Figure 3A:
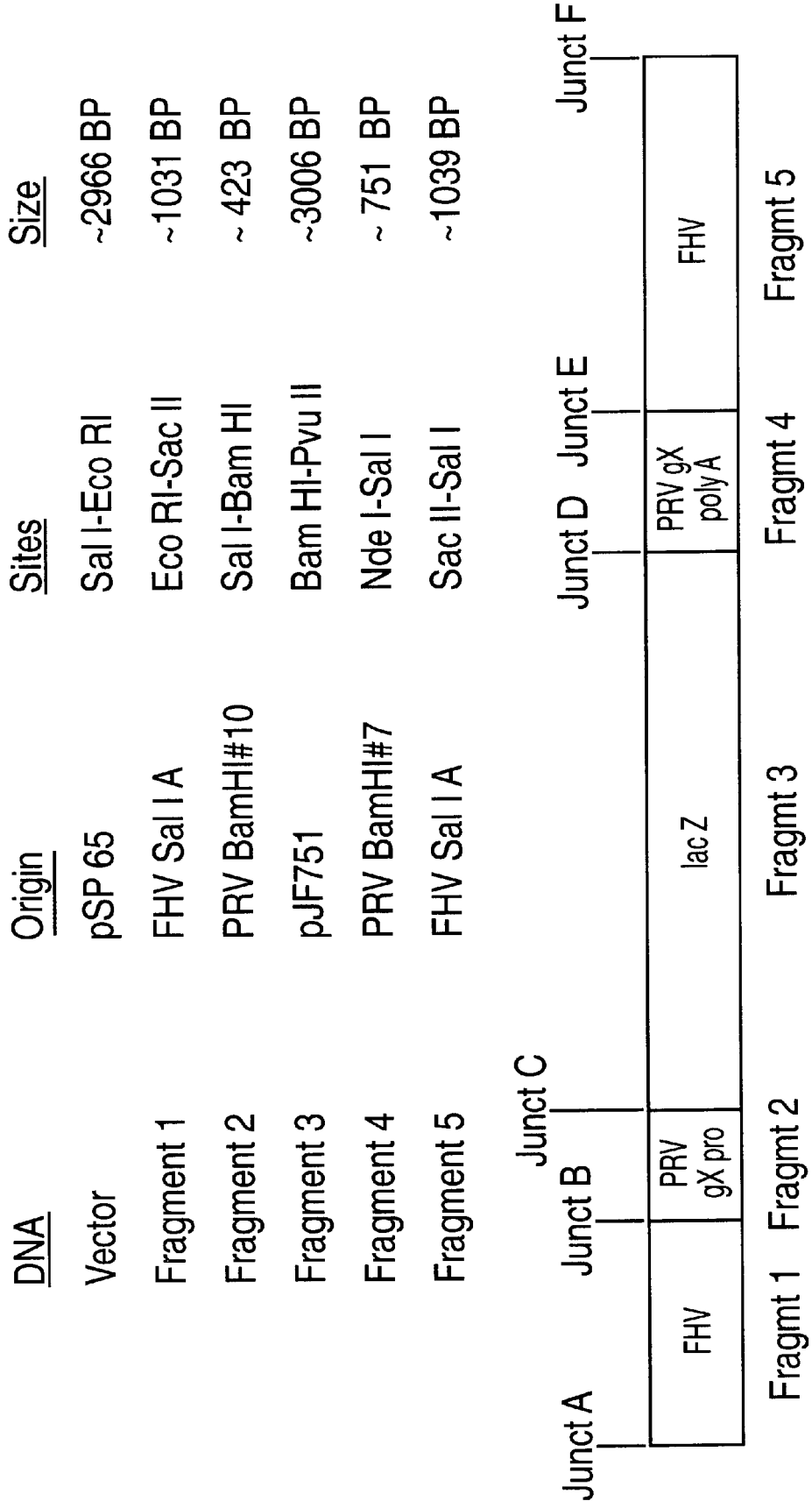

HOMOLOGY VECTOR 846-88.B7: The homology vector 846-88.B7 was constructed for the purpose of deleting a portion of the gE coding region from the feline herpesvirus and inserting a foreign DNA. The foreign DNA is under the control of the FHV glycoprotein E promoter. A detailed description of the plasmid is given in FIG. 3. It was constructed from the indicated DNA sources utlilizing standard recombinant DNA techniques [22, 23]. The plasmid vector is derived from an approximately 2958 base pair Asp718I restriction endonuclease fragment of a pSP18/pSP19 fusion such that the multiple cloning site is EcoRI/SacI/Asp718I/SacI/EcoRI. Fragment 1 is an approximately 1415 base pair Asp718I to SmaI subfragment of the FHV SalI B fragment which contains the FHV gE promoter. Fragment 2 is an approximately 3085 base pair fragment containing the lac Z DNA coding region was generated via PCR and synthetic primers, 5'-GCAACTG-CAGCAACAATGAATTCGGATCCCG-3' (6/96.18; SEQ ID NO. 21) and 5'CGTTCTGCAGCCTCTAGC-TTATTCTAGATCTTT-3' (6/96.19; SEQ ID NO. 22). These primers introduced an in-frame ATG and unique Pst I sites at both ends of the fragment. Fragment 3 is an approximately 2205 base pair SalI to Asp718I subfragment of FHV EcoRI E fragment.

EXAMPLE 1

Recombinant feline herpesvirus (FHV) containing a deletion of the entire gE gene and an insertion of a foreign DNA sequence into that site will replicate in cats and is useful as a vaccine. The ability to isolate a gE-deleted FHV confirms that the FHV gE gene (SEQ ID NOs: 1 and 2) is non essential for replication of the recombinant FHV. Recombinant FHV expressing foreign genes for viral, bacterial or parasite antigens protect against disease in dogs and cats. Recombinant FHV which was isolated contains a deletion of the gE gene within the unique short and an insertion of a foreign gene into that gE site or any non-essential site will replicate in cats and is useful as a vaccine.

Recombinant FHV containing a deletion of the gE gene within the unique short and an insertion of a foreign gene into that site is useful as a vaccine. Recombinant FHV expressing foreign genes for viral, bacterial, or parasite antigens is useful as a vaccine to protect against disease in cats, dogs, humans, horses, cattle, swine and poultry.

The sequence of the gE gene (SEQ ID NOS: 1 and 2) includes the coding sequence for the 531 amino acid open reading frame of the gE gene and also includes the SmaI site in the FHV SalI B fragment and the SalI site in the FHV EcoRI E fragment which define the endpoints of the deletion of the gE gene. To one side of the FHV gE deletion, homology vectors 416-80.21, 644-09.A1 and 644-09.B2 contain an approximately 1415 base pair Asp718I to SmaI subfragment of FHV SalI B containing the entire coding sequence of the gI gene (370 amino acids). To the opposite side of the FHV gE deletion, homology vector 416-80.21 contains an approximately 5200 base pair SalI to PvuII subfragment of the FHV EcoRI E fragment which contains unique short and terminal repeat sequences. To the opposite side of the FHV gE deletion in homology vectors 644-09.A1 and 644-09.B2, an approximately 2205 base pair SalI to Asp718I subfragment of the FHV EcoRI E fragment contains unique short and terminal repeat sequences.

EXAMPLE 2

Feline Herpesvirus Unique Long insertion sites: S-FHV-025 and S-FHV-026.

Feline Herpesvirus DNA (NVSL strain, also designated as S-FHV-001) was digested with SalI and the resulting fragments were cloned into the SalI site of pSP 65 (Promega Corp.) plasmid cloning vector. Plasmid 386-42.1B, a DNA clone identified as the SalI A fragment (~16 kb) of the FHV genome, was double digested with EcoRI and SalI, to create subfragments. A 3.0 kb EcoRI/Sal I subfragment of SalI A was isolated and subcloned, resulting in plasmid 860-85.A29. The 3.0 kb FHV EcoRI to SalI subfragment from this clone was sequenced by the method of fluorescent automated sequencing (ABI).

DNA sequence homology analysis determined that regions in the 3.0 kb EcoRI to SalI FHV subfragment contain homology to HSV-1 UL24, UL25 and the 5' region of UL26. The order of the open reading frames is: FHV thymidine kinase (TK) gene, UL24, UL25, UL26, and FHV gB gene.

A gene cassette containing the *E.coli* β-galactosidase coding region with the PRV gX promoter and the PRV gX polyadenylation regulatory signals was inserted into 860-85.A29 to facilitate the construction of two novel FHV homology vectors. One FHV homology vector designated 885-30.A4, contains gX promoter-lacZ-gX poly A inserted into a unique NdeI site. A second homology vector designated 885-30.F9 contains gX promoter-lacZ-gX poly A inserted into an 878 bp SacII deletion. The Nde I site and Sac II deletion interrupt a predicted open reading frame which has homology to HSV-1 UL 25.

Wild type FHV viral DNA (NVSL), combined with plasmid DNA, 885-30.A4 or 885-30.F9 was introduced into CRFK cells by the calcium phosphate transfection method. Recombinant plaques expressing β-galactosidase were identified from cotransfection stocks and isolated. Recombinant viruses, S-FHV-025 and S-FHV-026, are purified by several rounds of plaque passage and isolation.

S-FHV-025

S-FHV-025 is a recombinant feline herpesvirus that has an insertion of a foreign gene into a 3.0 kb EcoRI to SalI region of the SalI A genomic fragment of the FHV genome. The foreign DNA is inserted within a deletion of 878 base pairs between SacII sites (nucleotide 1049–1928, SEQ. ID. NO: 3) within the 3.0 kb EcoRI to SalI region. The *E. coli* lacZ (β-galactosidase) gene is under the transcriptional control of the PRV gX promoter.

S-FHV-025 was derived from S-FHV-001 (NVSL strain). This was accomplished utilizing the homology vector 885-30.A4 (see Materials and Methods) and virus S-FHV-001 in the HOMOLOGOUS RECOMBINATION PROCEDURE FOR GENERATING RECOMBINANT HERPESVIRUS. The transfection stock was screened by the SCREEN FOR RECOMBINANT HERPESVIRUS EXPRESSING ENZYMATIC MARKER GENES. The result of multiple rounds of blue plaque purification is the recombinant virus designated S-FHV-025.

This virus is characterized by restriction endonuclease mapping and the SOUTHERN BLOTTING DNA procedure to confirm the insertion of the *E. coli* lacZ (β-galactosidase)

gene. The virus is further characterized by BLACK PLAQUE ASSAY and WESTERN BLOT to confirm expression of the foreign DNA. S-FHV-025 is useful as a vaccine against feline rhinotracheitis and as a vector to express foreign DNA from disease-causing microorganisms (see Example 4) including but not limited to feline immunodeficiency virus and feline leukemia virus.

S-FHV-026

S-FHV-026 is a recombinant feline herpesvirus that has an insertion of a foreign gene into a 3.0 kb EcoRI to SalI region of the SalI A genomic fragment of the FHV genome. The foreign DNA is inserted into a unique NdeI site (nucelotide 1304–1309 SEQ. ID. NO:3) in the 3.0 kb EcoRI to SalI region. The *E. Coli* lacZ (β-galactosidase) gene is under the transcriptional control of the PRV gX promoter.

S-FHV-026 was derived from S-FHV-001 (NVSL strain). This was accomplished utilizing the homology vector 885-30.F9 (see Materials and Methods) and virus S-FHV-001 in the HOMOLOGOUS RECOMBINATION PROCEDURE FOR GENERATING RECOMBINANT HERPESVIRUS. The transfection stock was screened by the SCREEN FOR RECOMBINANT HERPESVIRUS EXPRESSING ENZYMATIC MARKER GENES. The result of multiple rounds of blue plaque purification is the recombinant virus designated S-FHV-026.

This virus is characterized by restriction endonuclease mapping and the SOUTHERN BLOTTING DNA procedure to confirm the insertion of the *E. coli* lacZ (β-galactosidase) gene and the deletion of the 878 base pair region between SacII sites. The virus is further characterized by BLACK PLAQUE ASSAY and WESTERN BLOT to confirm expression of the foreign DNA.

S-FHV-026 is useful as a vaccine against feline rhinotracheitis and as a vector to express foreign DNA from disease-causing microorganisms (see Example 4) including but not limited to feline immunodeficiency virus and feline leukemia virus.

EXAMPLE 3

Recombinant feline herpesvirus (FHV) expressing a foreign DNA sequence under the control of the FHV glycoprotein E promoter. An approximately 1415 base pair Asp718I to SmaI subfragment of the FHV SalI B fragment contains the FHV gE promoter. The FHV gE promoter is useful as an endogenous promoter in feline herpesvirus or as a heterologous promoter in other herpesviruses, such as pseudorabies virus, herpesvirus of turkeys, bovine herpesvirus, equine herpesvirus, canine herpesvirus, infectious laryngotracheitis virus, human cytomegalovirus, or poxviruses, such as fowlpox, canarypox, swinepox, raccoonpox, or vaccinia, or adenoviruses, or retroviruses.

S-FHV-020

S-FHV-020 is a recombinant feline herpesvirus that has a deletion of the gE gene and an insertion of one foreign gene at the gE deletion site. The *E. coli* lacZ (β-galactosidase) gene is under the transcriptional control of the FHV glycoprotein E (gE) promoter.

S-FHV-020 was derived from S-FHV-001 (NVSL strain). This was accomplished utilizing the homology vector 846-88.B17 (see Materials and Methods) and virus S-FHV-001 in the HOMOLOGOUS RECOMBINATION PROCEDURE FOR GENERATING RECOMBINANT HERPESVIRUS. The transfection stock was screened by the SCREEN FOR RECOMBINANT HERPESVIRUS EXPRESSING ENZYMATIC MARKER GENES. The result of multiple rounds of blue plaque purification is the recombinant virus designated S-FHV-026.

S-FHV-020 is useful as a vaccine against feline rhinotracheitis and as a vector to express foreign DNA from disease-causing microorganisms (see Example 4) including but not limited to feline immunodeficiency virus and feline leukemia virus. FHV 020 is useful as a parent virus to generate new FHV recombinants which do not contain a lac Z reporter gene.

EXAMPLE 4

Recombinant feline herpesvirus expressing antigens from disease causing microorganisms. In addition to recombinant feline herpesvirus expressing antigens from feline leukemia virus, feline immunodeficiency virus and *Dirofilaria immitis* (heartworm). Additional antigens from disease causing microorganisms in cats include, but art not limited to *Dirofilaria immitis* p39 and 22 kD antigens, feline infectious peritonitis virus, calicivirus, rabies, virus, feline parvovirus (panleukopenia virus), feline coronavirus and feline Chlamydia, *Toxoplasma gondii*. Disease causing microorganisms in dogs include, but are not limited to canine distemper, canine adenovirus type 1 (hepatitis), adenovirus type 2 (respiratory disease), parainfluenza, leptospira canicola, icterohemorragia, parvovirus, coronavirus, borrelia burgdorferi, canine herpesvirus, bordetella bronchiseptica and rabies virus.

Recombinant feline herpesviruses are useful for expressing antigens from disease causing microorganisms from animals in addition to dogs and cats. Recombinant feline herpesvirus is useful as a vaccine in animals including but not limited to humans, horses, cattle, swine and poultry.

Recombinant feline herpesvirus is useful as a vaccine against equine diseases when foreign antigens from the following diseases or disease organisms are expressed in the feline herpesvirus vector: equine influenza, equine herpesvirus-1 and equine herpesvirus-4. Recombinant feline herpesvirus is useful as a vaccine against bovine diseases when foreign antigens from the following diseases, or disease organisms are expressed in the feline herpesvirus vector: bovine viral diarrhea virus, bovine respiratory syncytial virus, bovine parainfluenza virus. Recombinant feline herpesvirus is useful as a vaccine against swine diseases when foreign antigens from the following diseases or disease organisms are expressed in the feline herpesvirus vector: pseudorabies virus, porcine reproductive and respiratory syndrome (PRRS/SIRS), hog cholera virus, swine influenza virus, swine parvovirus, swine rotavirus. Recombinant feline herpesvirus is useful as a vaccine against poultry diseases when foreign antigens from the following diseases or disease organisms are expressed in the feline herpesvirus vector: infectious bronchitis virus, Newcastle disease virus, infectious bursal disease virus, Marek's disease virus, infectious laryngotracheitis virus.

Recombinant feline herpesvirus is useful as a vaccine against human diseases. For example, human influenza is a rapidly evolving virus whose neutralizing viral epitopes are rapidly changing. A useful recombinant feline herpesvirus vaccine is one in which the influenza neutralizing eptiopes are quickly changed to protect against new strains of influenza. Human influenza HA and NA genes are cloned into the recombinant feline herpesvirus. Recombinant feline herpesvirus is useful as a vaccine against other human diseases when foreign antigens from the following diseases or disease organisms are expressed in the feline herpesvirus vector: hepatitis B virus surface and core antigens, hepatitis C virus, herpes simplex virus, human herpesviruses, herpes simplex virus-1, herpes simplex virus-2, human herpesvirus- 6, human herpesvirus-7, human cytomegalovirus, Epstein-Barr virus, Varicella-Zoster virus, human immunodeficiency virus, human influenza, measles virus, hantaan virus, pneumonia virus, rhinovirus, poliovirus, human respiratory syncytial virus, retrovirus, human T-cell leukemia virus, rabies virus, mumps virus, malaria (*Plasmodium falciparum*), *Bordetella pertussis*, Diptheria, *Rickettsia prowazekii, Borrelia bergdorferi*, Tetanus toxoid, malignant tumor antigens.

Recombinant feline herpesviruses coexpressing a species-specific cytokine and an antigen from a disease causing microorganism are useful to stimulate an increased cellmediated and humoral immune response in the animal and increases the efficacy of the recombinant feline herpesvirus as a vaccine. Cytokines which are expressed in feline herpesvirus include but are not limited to interleukin-1 through Interleukin-18, interferon, B7-1, B7-2 and granulocyte-macrophage colony stimulating factor.

REFERENCES

1. R. W. Price and A. Kahn, *Infection and Immunity*, 34, 571–580 (1981).
2. R. B. Tenser, et al., *Journal of Clinical Microbiology* 17, 122–127 (1983).
3. B. Roizman, et al., Cold Spring Harbor Conference on New Approaches to Viral Vaccines (September 1983).
4. K. Fukuchi et al., *Proc. Natl. Acad. Sci. U.S.A.* 82, 751–754 (1985).
5. J. M. Koomey et al., *Journal of Virology* 50, 662–665 (1984).
6. B. Lomniczi et al., *Journal of Virology* 49, 970–979 (1984).
7. R. A. Crandell and F. D. Maurer, *Proc. Soc. Exp. Biol. Med.* 97, 487–490 (1958).
8. R. M. Gaskell and R. C. Povey, *Res. Vet. Sci.* 27 167–174 (1978).
9. R. C. Povey, Microbiol. *Infect. Dis.* 2 373–387 (1979).
10. K. Tham and M. Studdert, *Veterinary Record* 120 321–326.
11. F. Fenner,. P. A. Bachmann, E. P. J. Gibbs, F. A. Murphy, M. J. Studdert and D. O. White, *Veterinary Virology*, Academic Press, Inc., (1987).
12. A. Grail, D. A. Harbour, W. Chia, Arch. *Virology* 116, 209–220 (1991).
13. P. A. Rota, R. K. Maes and W. T. Ruyechan, *Virology* 154, 168–179 (1986).
14. J. H. Nunberg, et al., *J. Virology* 63, 3240–3249 (1989).
15. Federal Register, Vol. 55, No. 90, pp. 19245–19253
16. R. W. Honess, *Journal of General Virology* 65, 2077–2107 (1984).
17. M. L. Cook & J. G. Stevens, *Journal of General Virology* 31, 75–80 (1976).
18. S. Joshi, et al., *Journal of Virology* 65, 5524–5530 (1991).
19. M. Wachsman, et al., *Journal of General Virology* 70, 2513–2520 (1989).
20. R. A. Bhat, et al., *Nucleic Acids Research* 17, 1159–1176 (1989)
21. J. H. Elder and J. I. Mullins, *Journal of Virology* 46 871–880 (1983).
22. T. Maniatis, et al., Molecular Cloning: A Laboratory Manual, Cold Spring Harbor, N.Y. (1982).
23. J. Sambrook, et al., *Molecular Cloning: A Laboratory Manual Second Edition*, Cold Spring Harbor Press, Cold Spring Harbor, N.Y. (1989).
24. M. A. Innis et al. *PCR Protocols: A Guide to Methods and Applications*, Academic Press, Inc., San Diego (1990).
25. Graham and Van der eb (1973), *Virology* 52, 556–557 (1973).
26. M. Zijil, et al., *Journal of Virology* 62, 2191–2195 (1988).
27. M. A. Wild, et al., 15th International Herpesvirus Workshop, Abstract No. 122, Washington, D.C. (1990).
28. F. A. Ferrari, et al., *Journal of Bacteriology* 161, 556–562 (1985).
29. B. Lomniczi et al., *Journal of Virology* 49 970–979 (1984).
30. D. J. McGeoch et al., *Journal of Molecular Biology* 181 1–13 (1985).
31. D. R. Thomsen et al., *Gene* 16 207–217 (1981).
32. T. R. Phillips, et al., *J. Virology* 64 4605–4613 (1990).
33. J. P. Ryan, et al., *J. Virology* 61 2962–2972 (1987).
34. J. A. Culpepper, et al., *Mol. Biochem. Parasitol.* 54 51–62 (1992).
35. J. E. Coligan, ed., *Current Protocols in Immunology* John Wiley & Sons, Inc. (1994)
36. G. C. Cole, et al., *J. Virology* 64 4930–4938 (1990).
37. R. L. Burke, *Seminars in Virology* 4 187–197 (1993).
38. T. C. Mettenleiter, *Comparative Immunology, Microbiology and Infectious Diseases* 14 151–163 (1991).
39. U. K. Laemnli, *Nature* 227, 680–685 (1970)
40. Willemse, et al., European application EP 576 092 A1.
41. Nunberg, et al., U.S. Pat. No. 5,324,664.
42. Post, et al., PCT International application WO 90/01547.
43. Sondermeijer, et al., PCT International application WO 94/03621
44. Maes, et al., PCT International application WO 95/00172
45. Willemse, et al., *Journal of General Virology*, 75, 3107–3116 (1994).

What is claimed is:

1. A recombinant feline herpesvirus comprising a foreign DNA inserted into a feline herpesvirus genome, wherein the foreign DNA is inserted into a region of the genome which corresponds to a 3.0 kb EcoRI-SalI fragment within a SalI A fragment of the feline herpesvirus genome and is capable of being expressed in a host cell into which the virus is introduced.

2. The recombinant feline herpesvirus of claim 1, wherein the foreign DNA is inserted within a UL25 gene within the region which corresponds to the 3.0 kb EcoRI-SalI fragment.

3. The recombinant feline herpesvirus of claim 1, wherein the foreign DNA is inserted within a NdeI site within the region which corresponds to the 3.0 kb EcoRI-SalI fragment.

4. The recombinant feline herpesvirus of claim 1, further comprising a second foreign DNA inserted within a non-essential region of the feline herpesvirus genome.

5. The recombinant feline herpesvirus of claim 4, wherein the second foreign DNA is inserted within a unique short region of the feline herpesvirus genome.

6. The recombinant feline herpesvirus of claim 4, wherein the second foreign DNA is inserted within a glycoprotein E gene within the unique short region of the feline herpesvirus genome.

7. The recombinant feline herpesvirus of claim 4, the second foreign DNA is inserted within a glycoprotein I gene within the unique short region of the feline herpesvirus genome.

8. The recombinant feline herpesvirus of claim 4, the second foreign DNA is inserted within a glycoprotein G gene within the unique short region of the feline herpesvirus genome.

9. The recombinant feline herpesvirus of claim 1, further comprising a deletion in a non-essential region of the feline herpesvirus genome.

10. The recombinant feline herpesvirus of claim 9, wherein the deletion is in the unique short region.

11. The recombinant feline herpesvirus of claim 1, wherein the foreign DNA encodes a screeneable marker.

12. The recombinant feline herpesvirus of claim 11, wherein the screenable marker is E. coli beta-galactosidase.

13. The recombinant feline herpesvirus of claim 11, wherein the screenable marker is E. coli beta-glucouronidase.

14. The recombinant feline herpesvirus of claim 1, wherein the foreign DNA encodes a polypeptide.

15. The recombinant feline herpesvirus of claim 1, wherein the- foreign DNA encodes Marek's Disease Virus glycoprotein A, Marek's Disease Virus glycoprotein B or Marek's Disease Virus glycoprotein D.

16. The recombinant feline herpesvirus of claim 1, wherein the foreign DNA encodes Newcastle Disease Virus fusion protein or Newcastle Disease Virus hemagglutinin-neuraminidase.

17. The recombinant feline herpesvirus of claim 1, wherein the foreign DNA encodes Infectious Laryngotracheitis Virus glycoprotein B Infectious Laryngotracheitis Virus glycoprotein I or Infectious Laryngotracheitis Virus glycoprotein D.

18. The recombinant feline herpesvirus of claim 1, wherein the foreign DNA encodes Infectious Bronchitis Virus spike protein or Infectious Bronchitis Virus matrix protein.

19. The recombinant feline herpesvirus of claim 1, wherein the foreign DNA encodes Infectious Bursal Disease virus VP2, Infectious Bursal Disease virus VP3, or Infectious Bursal Disease virus VP4.

20. The recombinant feline herpesvirus of claim 1, wherein the foreign DNA is selected from the group consisting of: Feline Leukemic virus envelope gene, Hepatitis B core antigen gene, Pseudorabies virus glycoprotein C gene, Dirofilaria immitis 22 kD gene, Dirofilaria immitis p39 gene, Feline Immunodeficiency virus gag gene, Feline Immunodeficiency virus pol gene, and Feline Immunodeficiency virus env gene.

21. The recombinant feline herpesvirus of claim 1, wherein the foreign DNA encodes a cytokine.

22. The recombinant feline herpesvirus of claim 1, wherein the foreign DNA is under the control of an endogenous upstream promoter.

23. The recombinant feline herpesvirus of claim 1, wherein the foreign DNA is under the control of a heterologous upstream promoter.

24. The recombinant feline herpesvirus of claim 23, wherein the promoter is selected from the group consisting of: Pseudorabies virus glycoprotein X promoter, Herpes Simplex Virus-1 alpha 4 promoter, Human Cytomegalovirus immediate early promoter, Marek's Disease Virus glycoprotein A promoter, Marek's Disease Virus glycoprotein B promoter, Marek's Disease Virus glycoprotein D promoter, Infectious Laryngotracheitis Virus glycoprotein B promoter, Infectious Laryngotracheitis Virus glycoprotein D promoter, and Bovine Herpesvirus-1.1 VP8 promoter and chicken anemia virus promoter.

25. The recombinant feline herpesvirus of claim 22, wherein the promoter is feline herpesvirus glycoprotein E promoter.

* * * * *